US012728141B2

(12) United States Patent
Beaudry et al.

(10) Patent No.: US 12,728,141 B2
(45) Date of Patent: Sep. 8, 2026

(54) EQUINE-SPECIFIC THERAPEUTIC COMPOSITIONS AND METHODS OF USE

(71) Applicant: EquiStem Technology, LLC, Scottsdale, AZ (US)

(72) Inventors: Christian Beaudry, Scottsdale, AZ (US); Jaehyun Kim, Scottsdale, AZ (US)

(73) Assignee: EQUISTEM TECHNOLOGY, LLC, Scottsdale, AZ (US)

( * ) Notice: Subject to any disclaimer, the term of this patent is extended or adjusted under 35 U.S.C. 154(b) by 245 days.

(21) Appl. No.: 18/511,853

(22) Filed: Nov. 16, 2023

(65) Prior Publication Data

US 2024/0156875 A1 May 16, 2024

Related U.S. Application Data

(60) Provisional application No. 63/383,981, filed on Nov. 16, 2022.

(51) Int. Cl.
*A61K 35/50* (2015.01)
*C12N 5/073* (2010.01)

(52) U.S. Cl.
CPC ............ *A61K 35/50* (2013.01); *C12N 5/0605* (2013.01)

(58) Field of Classification Search
CPC ...................................................... A61K 35/50
See application file for complete search history.

(56) References Cited

U.S. PATENT DOCUMENTS

2008/0046095 A1 2/2008 Daniel
2018/0126036 A1 5/2018 Early

FOREIGN PATENT DOCUMENTS

WO 2014167142 A1 10/2014

OTHER PUBLICATIONS

Duddy et al, Healing time of experimentally induced distal limb wounds in horses is not reduced by local injection of equine-origin liquid amnion allograft. American journal of veterinary research, (Jul. 13, 2022) vol. 83, No. 8. pp. 1-6 (Year: 2022).*

* cited by examiner

*Primary Examiner* — Qiuwen Mi
(74) *Attorney, Agent, or Firm* — NGUYEN TARBET IP LAW

(57) ABSTRACT

Equine-specific therapeutic compositions comprising placental-derived materials and methods of use, and method of producing said equine-specific therapeutic compositions that is clear, safe, and physiologically and biologically active liquid injectable. The tissue processing protocols described herein include methods for processing and decontaminating the incoming placental tissue and fluid having coloration and contaminants to produce a clear amnion and amniotic fluid injectable product while preserving postbiotics, proteins, exosomes, biocomponents and maintaining their physiological and biological properties.

19 Claims, 13 Drawing Sheets

FIG. 3

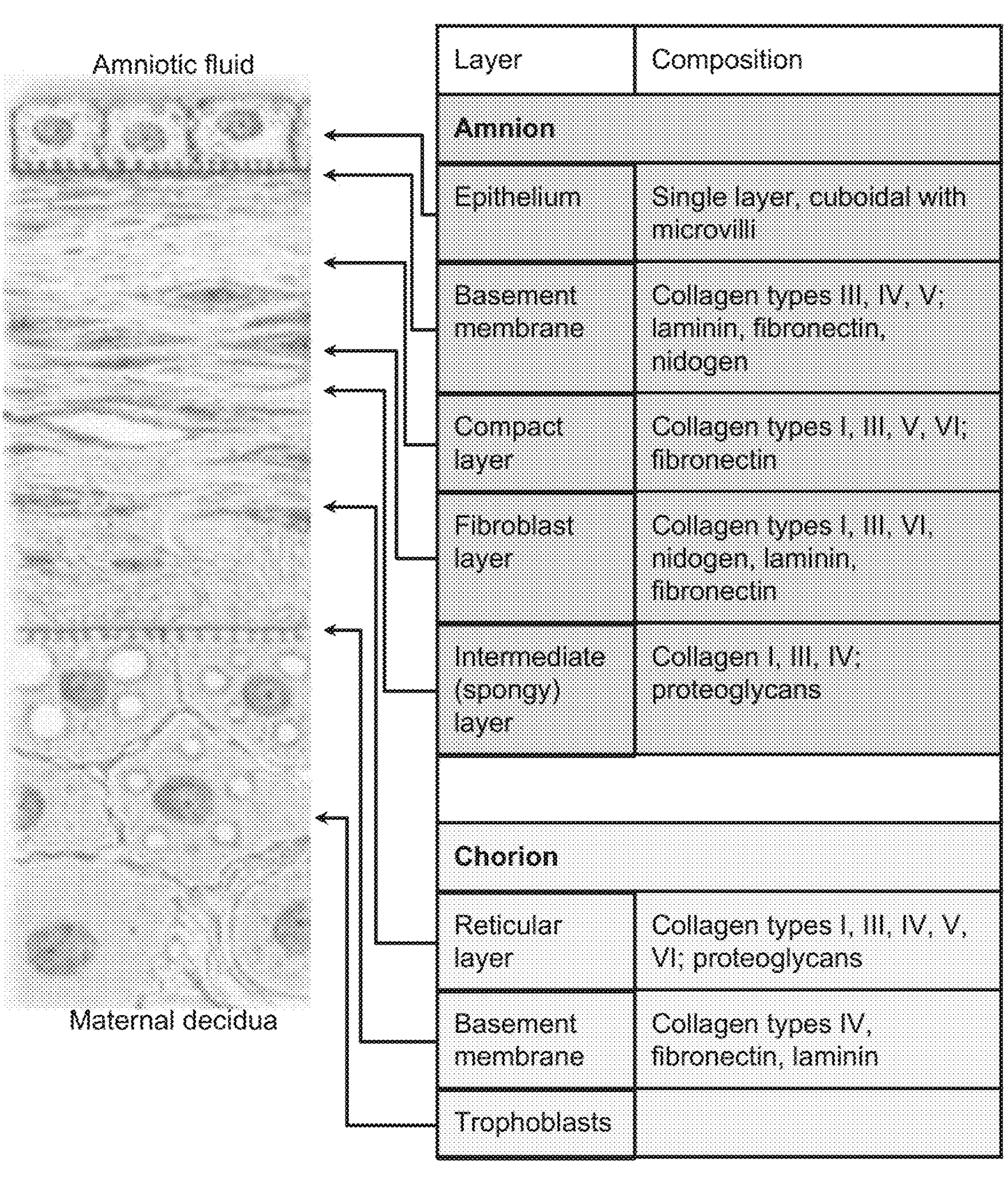

| Layer | Composition |
|---|---|
| **Amnion** | |
| Epithelium | Single layer, cuboidal with microvilli |
| Basement membrane | Collagen types III, IV, V; laminin, fibronectin, nidogen |
| Compact layer | Collagen types I, III, V, VI; fibronectin |
| Fibroblast layer | Collagen types I, III, VI, nidogen, laminin, fibronectin |
| Intermediate (spongy) layer | Collagen I, III, IV; proteoglycans |
| | |
| **Chorion** | |
| Reticular layer | Collagen types I, III, IV, V, VI; proteoglycans |
| Basement membrane | Collagen types IV, fibronectin, laminin |
| Trophoblasts | |

FIG. 5

| Microorganisms Found Present On The Allantoamnion Membrane | | |
|---|---|---|
| Acinetobacter baumanii | Enterobacter cloacae complex | Myroides species |
| Acinetobacter gandensis | Enterococcus casseliflavus | Pantoea agglomerans |
| Acinetobacter iwofii | Enterococcus avium | Pantoea species |
| Acinetobacter pseudolwoffii | Enterococcus gallinarum | Pasteurella canis |
| Acinetobacter species | Enterococcus hirae | Pseudomonas flourescens |
| Acinetobacter ursingii | Enterococcus mundtii | Pseudomonas putida |
| Acinetobacter variabilis | Escherichia coli | Pseudomonas species |
| Aerococcus viridans | Escherichia hermannii | Pseudomonas stutzeri |
| Aeromonas hydrophila | Gallolyticus | Psychrobacter faecalis |
| Aeromonas caviae | Globicatella anguiis | Psychrobacter pulmonis |
| Alcaligenes faecalis | Globicatella sulfidifaciens | Psychrobacter species |
| Arthrobacter species | Globicatella species | Raoultella planticola |
| Bacillus not anthracis | Gram Negative Rod | Serratia grimesii |
| Beta hemolytic Streptococcus group C | Klebsiella aerogenes | Serratia liquiefaciens |
| Brevunimonas diminuta | Klebsiella oxytoca | Serratia proteamaculans |
| Brevunimonas vesicularis | Klebsiella pheumoniae | Sphingobacterium species |
| Burkholderia cepacia complex | Klebsiella variicola | Sphingomonas paucimobilis |
| Calcoaceticus complex | Kocuria rhizophila | Staphylococcus arlettae |
| Candida famata | Kocuria rosea | Staphylococcus equorum |
| Candida zeylanoides | Kosakonia cowanii | Staphylococcus infantarius |
| Capnocytophaga species | Lactobacillus species | Staphylococcus lentus |
| Citrobacter amalonaticus | Lactococcus garvieae | Staphylococcus lutetiensis |
| Citrobacter species | Lactococcus lactis | Staphylococcus xylosus |
| Coagulase negative Staphylococcus | Lactococcus raffinolactis | Stenotrophomonas maltophilia |
| Comamonas sediminis | Lactococcus species | Streptococcus alactolyticus |
| Corynebacterium ammoniagenes | Leclercia adecarboxylata | Streptococcus dysgalactiae |
| Corynebacterium glutamicum | Luyvera intermedia | Streptococcus equi |
| Coryneform bacteria | Mixta calida | Streptococcus equinus |
| Enterococcus faecalis | Mixta gaviniae | Streptococcus pyogenese |
| Enterococcus faecium | Myroides odoratus | Weissella cibaria |
| **Microorganisms Found Present In The Amniotic Fluid** | | |
| Acinetobacter species | Coryneform bacteria | Gram negative rod |
| Aerococcus species | Cryptococcus uniguttulatus | Gram positive Cocci |
| Aerococcus urinaeequi | Cutibacterium acnes | Group D Enterococcus |
| Aerococcus viridans | Debaryomyces hansenii | Kocuria rosea |
| Alpha-hemolytic streptococcus | Enterococcus casseliflavus | Lactobacillus species |
| Bacillus not anthracis | Enterobacter cloacae complex | Microbacterium aerolatum |
| Brachybacterium conglomeratum | Enterococcus asini | Pseudarthrobacter species |
| Brachybacterium paraconglomeratum | Enterococcus casselifavus | Sphingobacterium species |
| Brachybacterium species | Enterococcus gallinarum | Staphylococcus aureus |
| Candida famata | Enterococcus species | Staphylococcus equorum |
| Candida zeylanoides | Finegoldia species | Staphylococcus sciuri |
| Citrobacter sedlakii | Gamma Hemolytic | Staphylococcus succinus |
| Coagulase negative Staphylococcus | Globicatella anguinis | Streptococcus not Enterococcus |
| Corynebacterium ammoniagenes | Globicatella species | Yeast |
| Corynebacterium species | | |

FIG. 6

| Protein | Finished Product | |
|---|---|---|
| | Low Concentration pg/mL | High Concentration pg/mL |
| A2M | 45,626 | 53,525 |
| TIMP-2 | 203,210 | 331,550 |
| TGF-b1 | 2,107 | 6,932 |
| $IFN_{\gamma}$ | 0.0 | 9.9 |
| IL-1a | 0.1 | 7.7 |
| IL-1b | 0.0 | 0.0 |
| IL-1ra | 6,882.8 | 30,177.0 |
| IL-2 | 0.0 | 1.8 |
| IL-4 | 0.0 | 4.2 |
| IL-8 | 1.2 | 40.8 |
| IL-10 | 5.6 | 79.2 |
| IL-15 | 0.0 | 19.9 |
| MCP-1 | 558.8 | 782.7 |
| VEGF | 20.1 | 82.8 |

| | exosomes/mL of product |
| --- | --- |
| Finished Product | 3,285,714 |

Finished Product 1
Finished Product 2
Finished Product 3

Cumulative protein release (mg/mL)

1.0
0.8
0.6
0.4
0.2
0.0

0 2 4 6 8 10 12 14 16 18 20 22 24

Time (day)

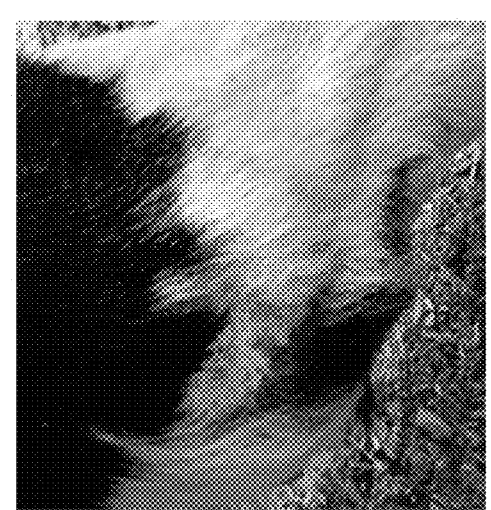
FIG. 14C
FIG. 14B
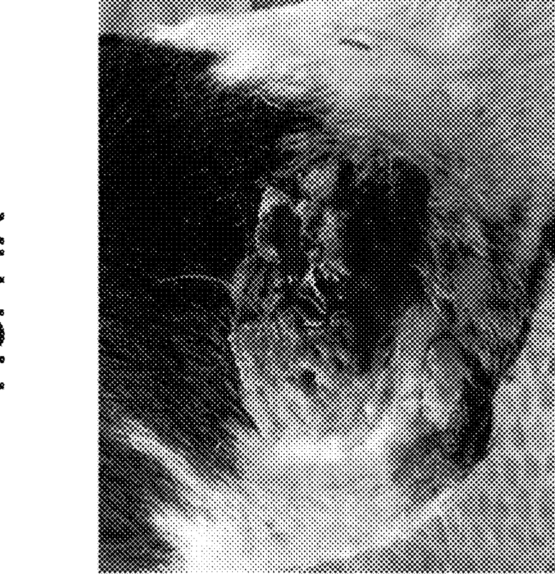
FIG. 14A

EQUINE-SPECIFIC THERAPEUTIC COMPOSITIONS AND METHODS OF USE

CROSS-REFERENCES TO RELATED APPLICATIONS

This application is a non-provisional and claims benefit of U.S. Provisional Application No. 63/383,981 filed Nov. 16, 2022, the specification of which is incorporated herein in their entirety by reference.

FIELD OF THE INVENTION

The present invention features equine-specific therapeutic compositions comprising placental-derived materials and methods of use.

BACKGROUND OF THE INVENTION

Horses are members of a group of species with diffuse placentas, meaning that nearly the entire surface of the chorioallantois is involved in forming the placenta. The equine placenta is composed of the umbilical cord and two distinct sacs: the chorioallantoic sac, which is the outer sac containing allantoic fluid, and the allantoamnion or amnion sac, which is the inner sac containing the amniotic fluid, and fetus.

The use of the placenta has been well explored for a variety of medical conditions, with many of these treatments illustrating superior healing and regenerative effects. This is because the equine placenta and fluid are a rich source of biological factors such as growth factors, cytokines, peptides, lipids, exosomes, mRNA, miRNA, and associated proteins involved in fetus development and with known anti-inflammatory, anti-fibrotic, immunomodulatory, tissue healing, and tissue repair properties.

The present invention has identified and yielded another biocomponent called postbiotics (in the product) that is safe and supports regenerative and healing capacity. Postbiotics originated from live/dead microorganisms that are naturally present in the equine placenta, including any substance released by or produced through the metabolic activity of the microorganisms or fragments of microorganisms. Postbitotics exert a beneficial effect on the host, including immunomodulatory, anti-inflammatory, antioxidant, and anti-cancer properties, directly or indirectly. For example, postbiotics can stimulate immune cells to secrete signaling molecules involved in tissue healing and repair. They can also modulate an immune response by inducing immune cells to kill tumor cells directly or reversing the immunosuppressive microenvironment, thus providing antitumor immunity. As postbiotics do not contain live microorganisms, the risks associated with their intake are minimized.

With the natural presence of such a wide variety of biocomponents, the equine placental tissue is an attractive source for the development of novel equine-specific biological products; however, the presence of contaminants, including blood-related contaminants, amniotic plaques, and large amounts of microorganisms naturally present in the equine placental tissue and fluid or acquired during tissue collection poses significant manufacturing challenges. Such contaminants may trigger alloimmunization responses in equine allograft recipients, thus harming the recipient and/or causing graft failure, adverse events, and decreasing or negating the therapeutic effects of the allograft materials. As such, a novel decontaminating method capable of removing or neutralizing contaminants in the equine-placental tissue while preserving its biocomponents and their biological and therapeutic properties is highly desired. Removal of contaminants allows genetically non-identical equine patient-recipients to receive allografts more safely and effectively, as the risk of alloimmunization reaction, adverse events, and graft rejection is reduced or eliminated.

The present invention features novel therapeutic composition and processing method designed to efficiently eliminate contaminants from equine placental tissue, yielding a product that is not only substantially clear and devoid of viable microorganisms but also preserves essential postbiotics (including metabolites, biopolymers, enzymes, short-chain fatty acids, bacterial lysates, and cell-wall fragments from decontaminated, non-viable microorganisms and their derivatives) as well as biocomponents (such as proteins, growth factors, cytokines, peptides, lipids, exosomes, mRNA, and miRNA), either individually or in combination.

BRIEF SUMMARY OF THE INVENTION

It is an objective of the present invention to provide compositions and methods that allow for the production of a clear, safe, and physiologically and biologically active liquid injectable product (i.e., an equine-specific therapeutic composition) for use as a regenerative product in horses with joint diseases, soft tissue lesions, inflammatory diseases, respiratory diseases, immunological diseases, cancer, neurological diseases, scarring, burns, wounds, eye ulcers, nerve injuries, muscle tears, organ diseases, among others, as specified in the independent claims. The present invention may also be administered via other routes of administration in other embodiments, for example, topically, intravenously, and by inhalation. Embodiments of the invention are given in the dependent claims. Embodiments of the present invention can be freely combined with each other if they are not mutually exclusive.

The present invention may feature a therapeutic composition comprising an allantoamnion membrane comprising allantoamnion specific postbiotics and a carrier solution, wherein the carrier solution comprises amniotic fluid comprising amniotic fluid specific postbiotics. In some embodiments, the present invention features an equine-specific therapeutic composition. The composition may comprise placental tissue (e.g., equine-specific placental tissue) in a carrier fluid. In some embodiments, the placental tissue comprises an allantoamnion, a chorioallantois, an amniotic fluid, an allantoic fluid, an umbilical cord, Wharton's Jelly, or a combination thereof. In certain embodiments, In other embodiments, the present invention features an equine-specific therapeutic composition comprising an equine-specific allantoamnion membrane comprising allantoamnion specific postbiotics and a carrier solution, wherein the carrier solution comprises equine-specific amniotic fluid comprising amniotic fluid specific postbiotics. In some embodiments, the composition is derived or made from placental tissue or fluid from a human, horse, canine, feline, porcine, bovine, camel, or the like.

The aforementioned therapeutic composition may further comprise proteins, growth factors, cytokines, peptides, lipids, exosomes, nucleic acids, DNA, mRNA, and miRNA derived from allantoamnion membrane particles, chorioallantois membrane particles, umbilical cord, Wharton's Jelly or a combination thereof and/or proteins, growth factors, cytokines, peptides, lipids, exosomes, nucleic acids, DNA, mRNA, and miRNA derived from the amniotic fluid, allantoic fluid, or a combination thereof. Additionally, the composition may be free or substantially free of contaminants including but are not limited to, blood-related components (e.g., plasma, red blood cells, white blood cells, platelets, wastes), immunogenic blood-related components, microorganisms (e.g., bacteria, e.g., aerobic bacteria or anaerobic bacteria, or viruses), fungi (e.g., yeast) or a combination thereof. The contaminants may further include byproducts of hemoglobin metabolism and/or catabolism, e.g., iron, heme, globin, biliverdin, bilirubin, or alternatively include products of hemoglobin breakdown.

In other embodiments, the present invention may further feature a method of producing an equine-specific therapeutic composition. The method may include obtaining a whole equine placenta and dissecting the whole equine placenta and retaining an allantoamnion membrane. The method may further comprise recovering equine amniotic fluid, e.g., from the whole equine placenta.

In some embodiments, the method comprises processing the allantoamnion membrane, the amniotic fluid, or both the allantoamnion membrane and the amniotic fluid. Processing the amniotic fluid may comprise centrifuging the amniotic fluid, decontaminating the amniotic fluid, and filtering the amniotic fluid. The aforementioned amniotic fluid may then be added to a carrier fluid. In some embodiments, the carrier fluid comprising the processed amniotic fluid may comprise amniotic fluid specific concentration of growth factors, cytokines, peptides, lipids, exosomes, mRNA, miRNA, postbiotics, and associated proteins. Moreover, processing the allantoamnion membrane may comprise rinsing, cleaning, and/or decontaminating the allantoamnion membrane to remove contaminants such as the blood vessels or amniotic plaques from the allantoamnion membrane. In some embodiments, processing the allantoamnion membrane further comprises drying the allantoamnion membrane. The processed allantoamnion membrane may then by micronized, e.g., to produce micronized allantoamnion membrane particles. In some embodiments, the aforementioned micronized allantoamnion membrane provides an allantoamnion membrane specific concentration of growth factors, cytokines, peptides, lipids, exosomes, mRNA, miRNA, postbiotics, and associated proteins. In some embodiments, the micronized allantoamnion membrane is resuspended into the carrier solution comprising the amniotic fluid to create an equine-specific therapeutic composition. In other embodiments, the method further comprises freezing the equine-specific therapeutic composition to preserve postbiotics and biocomponents.

In further embodiments, the present invention may further feature a method of treating or preventing cancer in an individual (e.g., an equine). The method may include administering a therapeutic amount of the aforementioned equine-specific therapeutic composition comprising placental tissue and a carrier fluid comprising amniotic fluid.

The histological representation of the equine allantoamnion membrane is distinct from the human amnion membrane. For example, the human fetal membrane is derived from the inner and outer layers of a single amniotic sac and is comprised of two conjoined membranes-amnion and chorion. The amnion faces the fetus, and the chorion faces the uterus. Contrastingly, in horses, the amnion membrane is part of the allantoamnion sac, which contains the fetus and amniotic fluid, and the chorion membrane is part of the chorioallantoic sac, which contains the allantoic fluid. The allantoamnion membrane comprises an epithelium layer and a basement membrane layer on both sides of a stroma layer. The allantoamnion membrane composition comprises cells, cellular excretions, cellular derivatives, and extracellular matrix components. The allantoamnion membrane is not attached to the chorionallantois, unlike the human amnion and chorion membranes.

Additionally, equine placentas and fluids contain a unique microbiome critical to foal development. Bacterial, fungal, and yeast cross-contamination of the placentas and fluid during placental tissue recovery at the time of foaling can also occur. While such microbiome is important during pregnancy, the microbiome and cross-contamination could be harmful if part of an injectable biological product. Thus, one of the unique and inventive technical features of the present invention is the decontamination process that is applied to both the tissue (e.g., the allantoamnion membrane) and the fluid (e.g., the amniotic fluid), which avoids the use of harsh processing or sterilization methods. The decontamination process used herein allows for the removal of contaminants from the composition while preserving postbiotics, growth factors, cytokines, peptides, lipids, exosomes, mRNA, miRNA, and proteins derived from both tissue and fluid. Without wishing to limit the invention to any theory or mechanism, it is believed that the technical feature of the present invention advantageously provides for a safe and effective equine-specific therapeutic composition comprising a high concentration of allantoamnion membrane and amniotic fluid-specific postbiotics, growth factors, cytokines, peptides, lipids, exosomes, mRNA, miRNA, and associated proteins.

Furthermore, the implemented decontamination process not only facilitates the preservation and utilization of all layers within the allantoamnion membrane but also ensures the elimination of contaminants from the composition that could potentially trigger an alloimmunization response when introduced to an individual (e.g., an equine patient). This includes the removal of various contaminants, with a specific focus on blood-related contaminants and microorganisms. Notably, blood group antigens, a significant category of alloantigens, are effectively removed by the decontamination of the present invention. The advantage of selectively removing these potentially immunogenic contaminants contributes to increased safety and efficacy in the composition. The reduction in the likelihood of alloimmune responses is crucial for heightened safety, given the potential consequences such responses can have, such as transfusion reactions, graft rejection, and other adverse effects that could directly harm the individual (e.g., the equine patient). Furthermore, the increased efficacy stems from a significant reduction in the probability of graft rejection, thereby enhancing the likelihood that the allograft can exert a therapeutic effect on the recipient (e.g., the equine patient-recipient).

None of the presently known prior references or work has the unique, inventive technical feature of the present invention. For example, human placentas and fluids lack a distinctive microbiome, rendering a decontamination process for microbiome removal, such as native microorganisms, unnecessary. Consequently, comparable human products lack the distinctive feature of postbiotics in their composition.

Furthermore, the inventive technical features of the present invention contributed to a surprising result. For example, the Inventors surprisingly found the presence of postbiotics on the allantoamnion tissue. Moreover, the applied processing methods, targeting both the tissue (e.g., placental tissue or allantoamnion membrane) and the amniotic fluid, not only effectively eradicate viable microorganisms but also safeguard crucial postbiotic components, including metabolites, biopolymers like exopolysaccharides, enzymes, short-chain fatty acids, bacterial lysates, and cell-wall fragments derived from decontaminated, non-viable microorganisms and their derivatives.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIG. 3 shows the different layers of the human amniotic membrane.

FIG. 5 shows non-limiting examples of microorganisms found present on the allantoamnion membrane and amniotic fluid from various tissue donors prior to processing and decontamination.

FIG. 6 shows non-limiting examples of proteins and their concentrations that may be within the equine-specific therapeutic composition described herein after processing (e.g., contained in the finished product). In some embodiments, the equine-specific therapeutic composition described herein may comprise alpha-2-macroglobulin (A2M), tissue inhibitor of metalloproteinases 2 (TIMP2), transforming growth factor beta-1 (TGF-b1), interferon-gamma (IFN-γ), interleukin-1 alpha (IL-1a), interleukin-1 beta (IL-1b), interleukin-1 receptor antagonist (IL-1ra), interleukin-2 (IL-2), interleukin-4 (IL-4), interleukin-8 (IL-8), interleukin-10 (IL-10), interleukin-15 (IL-15), monocyte chemoattractant protein-1 (MCP-1/CCL2), vascular endothelial growth factor (VEGF), or a combination thereof.

Figure 1:
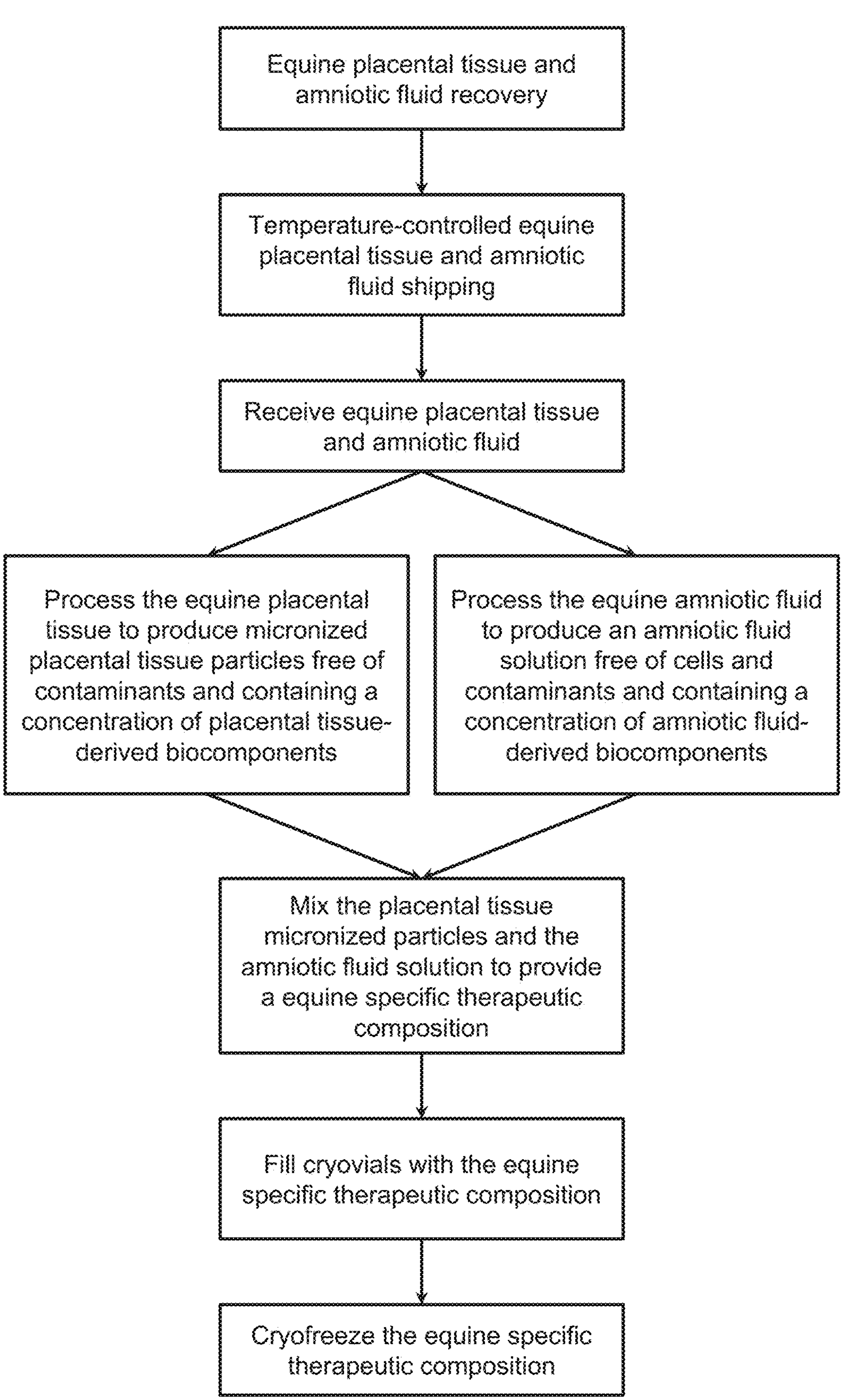
FIG. 1 shows a non-limiting example of how an equine-specific therapeutic composition may be processed.
Figure 2:
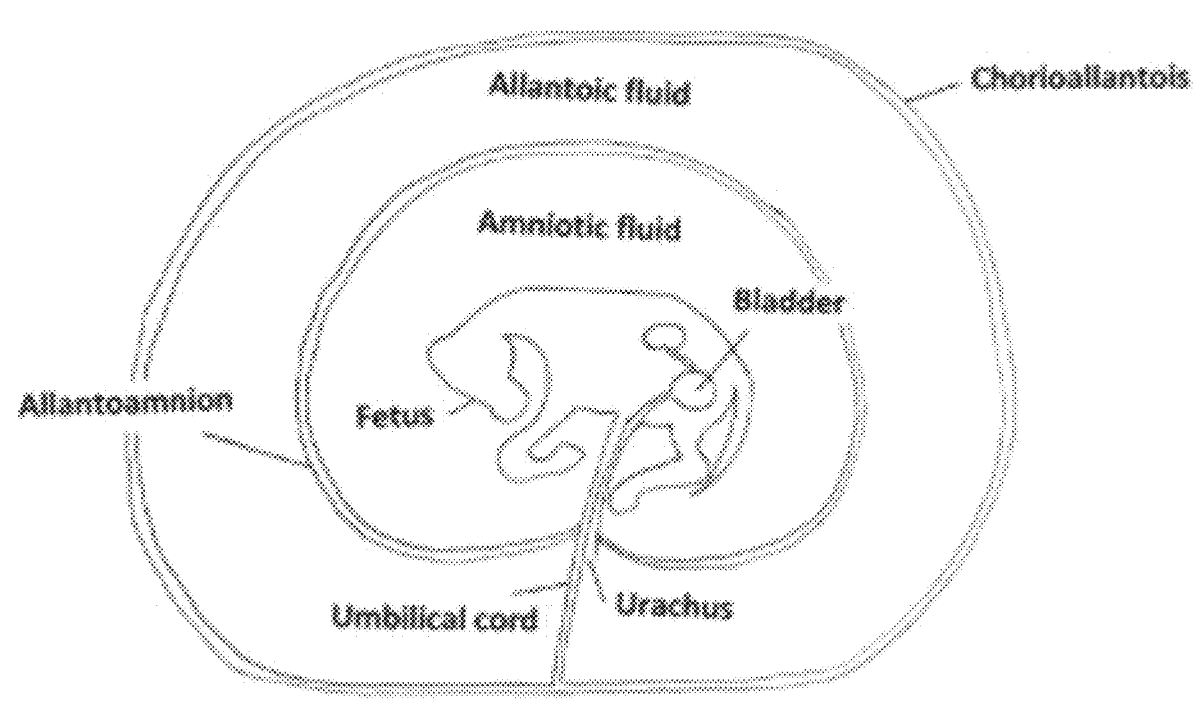
FIG. 2 shows an equine placenta comprising different sacs and fluids.
Figure 4:
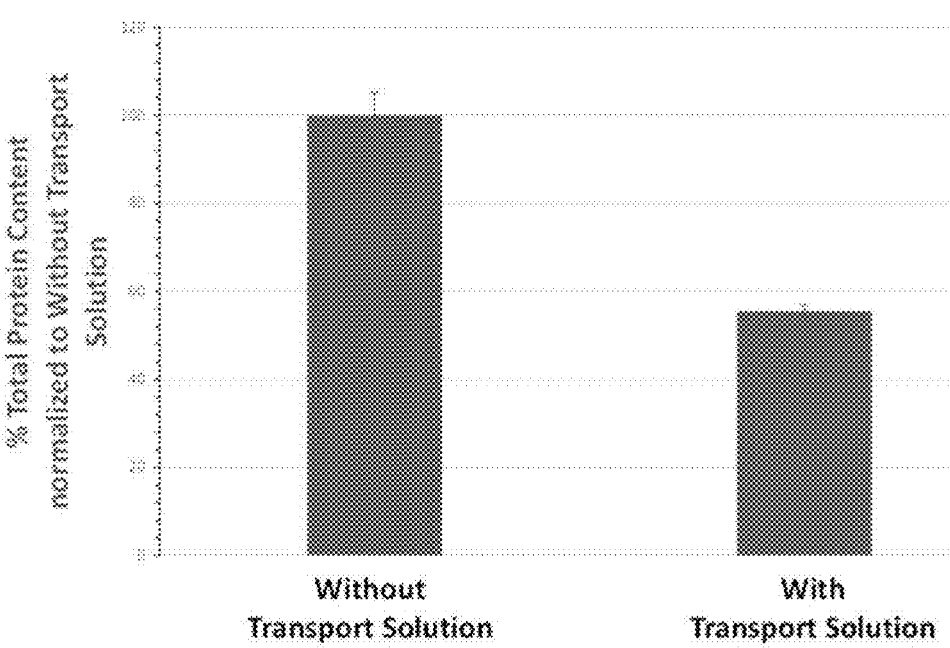
FIG. 4 shows that approximately 40% more proteins are retained in the membrane of the placenta when transported without a transport solution, according to the methods of the present invention, than when the placenta is transported with a transport solution.
Figures 7A, 7B, 7C:
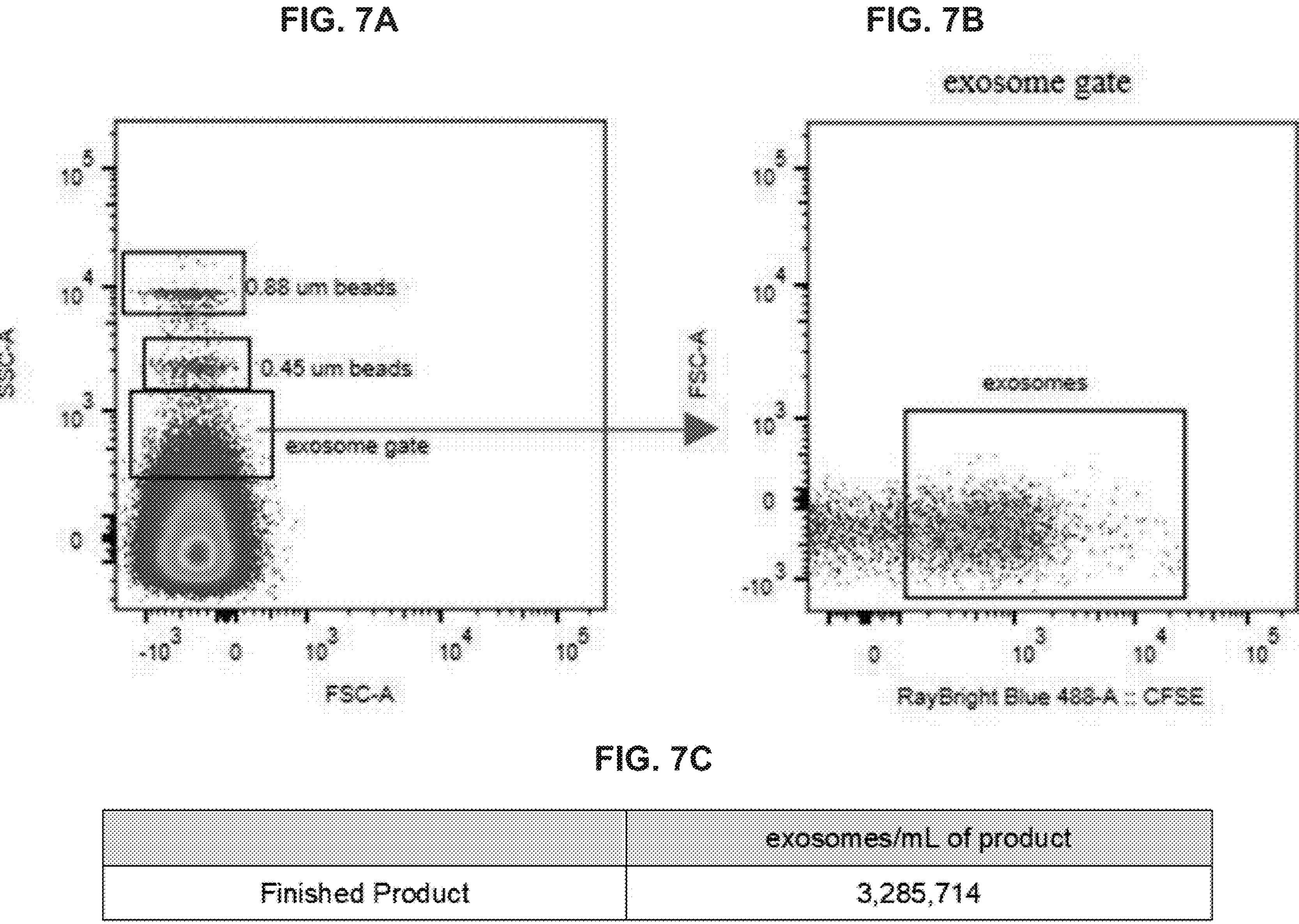

FIGS. 7A, 7B, and 7C shows flow cytometry analysis of exosomes contained within one sample of the finished product (e.g., equine-specific therapeutic composition). FIG. 7A shows a side scatter and forward scatter plot showing exosomes population based on size. FIG. 7B shows a scatter plot showing exosomes population based on positive staining. FIG. 7C shows a table showing exosomes concentration in the finished product.

Figure 8:
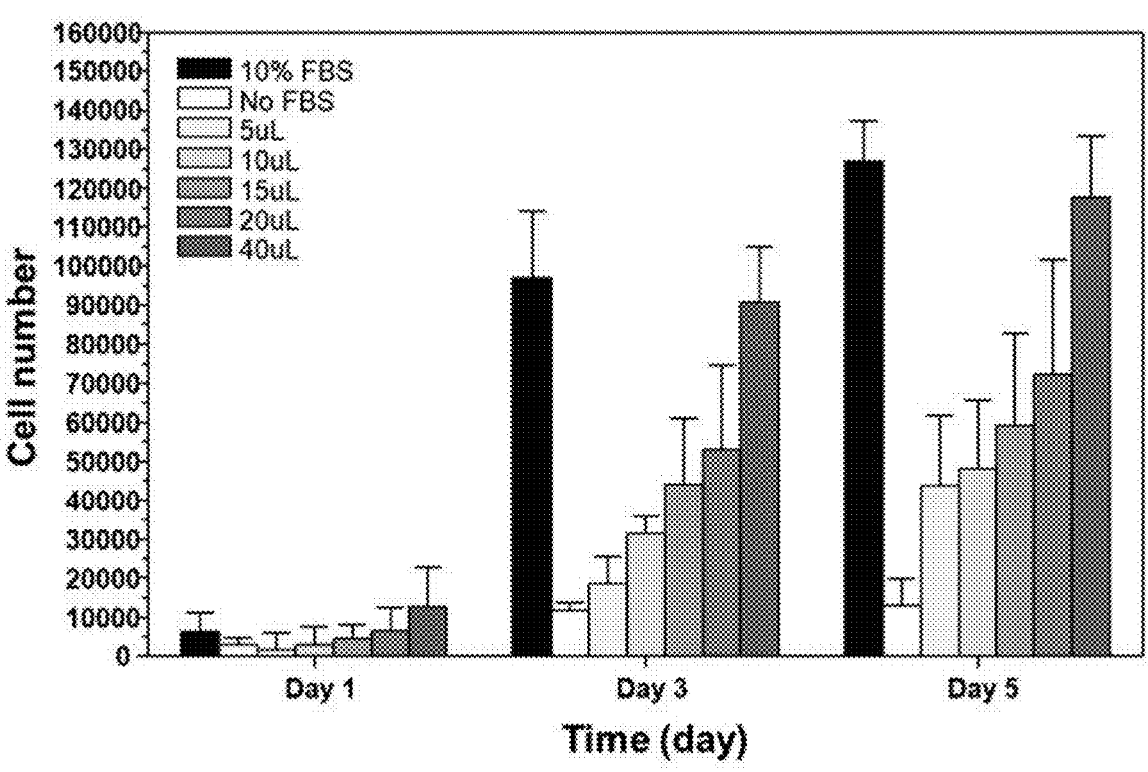

FIG. 8 shows the proliferation of dermal fibroblast when treated with an increasing amount of finished product. Either 5 uL, 10 uL, 15 uL, 20 uL, and 40 uL of finished product was added to either 95 uL, 90 uL, 75 uL, 80 uL, and 60 uL of cell culture media respectively. 10% fetal bovine serum (FBS) was added to cell culture media as positive control. Cell culture media alone without FBS was used as a negative control. Proteins contained within the finished product stimulated fibroblast cell proliferation in a dose-dependent manner.

Figure 9:
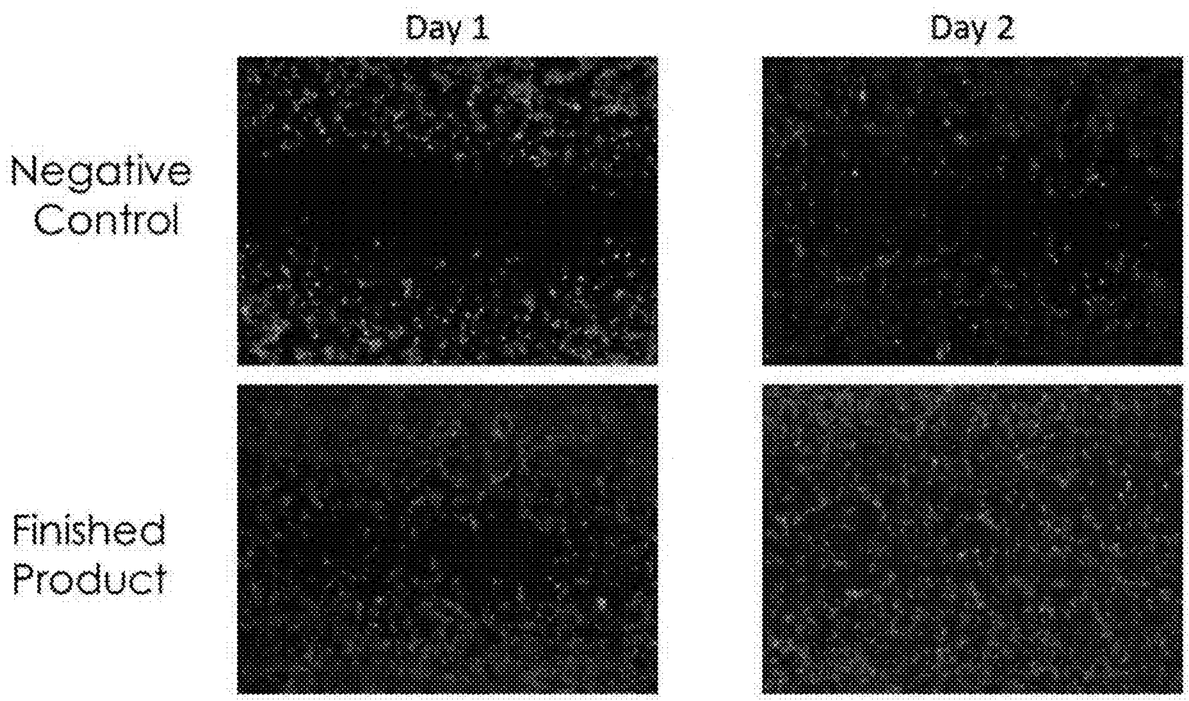

FIG. 9 shows the migration of dermal fibroblast using a scratch wound assay. Cell culture media alone without FBS was used as a negative control. 40 uL of finished product was added to 60 uL cell culture media alone. Proteins contained within the finished product stimulated fibroblast cell migration compared to negative control.

Figures 10, 11A, 11B, 11C:
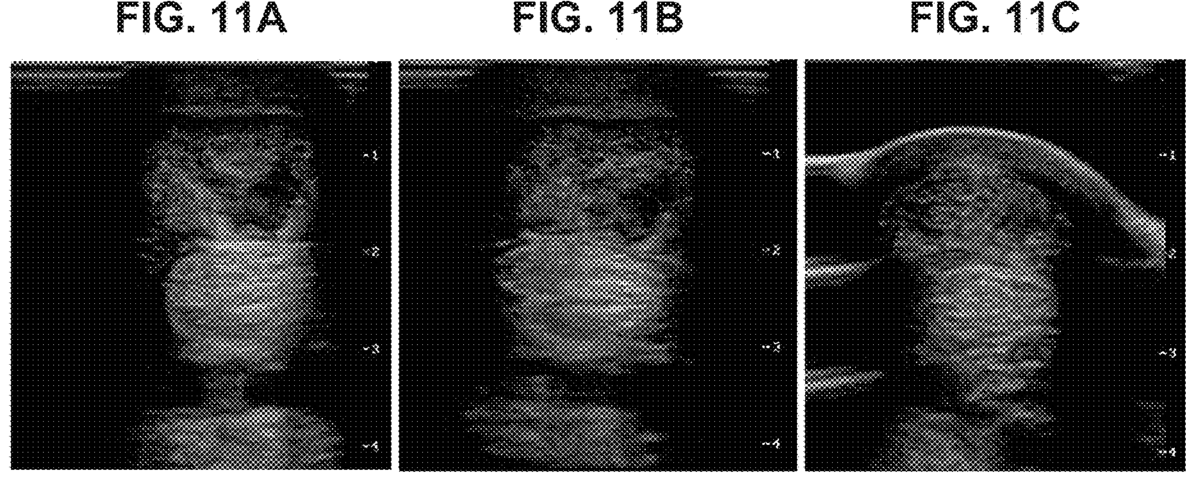

FIG. 10 shows protein elution from the allantoamnion micronized particles in the finished product over time. The finished product was incubated at 37° C. for 23 days. Protein release from the micronized particles was measured at different time points.

Figure 12C:
Figure 12B:
Figure 12A:

FIGS. 11A, 11B, and 11C show the effects of the finished product (e.g., equine-specific therapeutic composition) on tendon healing. FIG. 11A shows a chronic superficial digital flexor tendon core lesion before the injection of 1.5 mL of the equine-specific composition into the lesion. FIG. 11B shows chronic superficial digital flexor tendon core lesion one month after injection of the equine-specific composition. FIG. 11C shows chronic superficial digital flexor tendon core lesion three months after injection FIGS. 12A, 12B, and 12C show the effect of the finished product (e.g., equine-specific therapeutic composition) on wound healing. FIG. 12A shows a hoof wound on the day of subcutaneous injection of 3.0 mL of the equine-specific composition around the margin of the lesion. FIG. 12B shows the hoof wound one week after the subcutaneous injection of the equine-specific composition around the margin of the lesion. FIG. 12C shows the hoof wound six weeks after the subcutaneous injection of the equine-specific composition around the margin of the lesion.

Figure 13C:
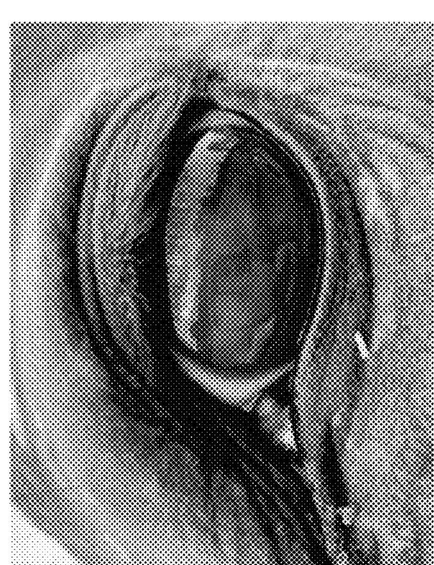
Figure 13B:
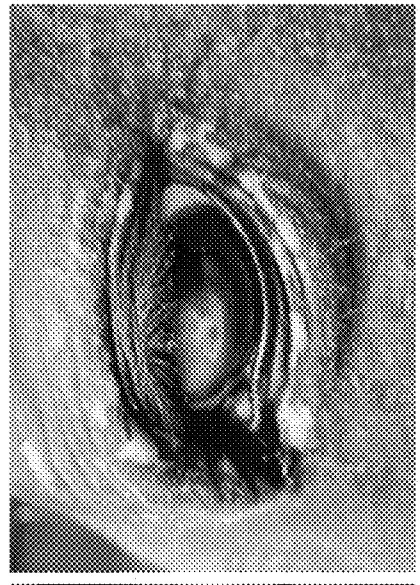
Figure 13A:

FIGS. 13A, 13B, and 13C show the effect of the finished product (e.g., equine-specific therapeutic composition) on eye ulcer healing. FIG. 13A shows an eye ulcer on the day of subconjunctival injection of 1.0 mL of the equine-specific composition. FIG. 13B shows the eye ulcer ten days after the subconjunctival injection of the equine-specific composition injection. FIG. 13C shows the eye ulcer four weeks after the subconjunctival injection of the equine-specific composition injection.

FIGS. 14A, 14B, and 14C show the effects of the finished product (e.g., equine-specific therapeutic composition) on sarcoid healing. FIG. 14A shows a sarcoid on the day of subcutaneous injection of 3.0 mL of the equine-specific composition around the margin of the sarcoid. FIG. 14B shows the sarcoid one month after the subcutaneous injection of the equine-specific composition around the margin of the sarcoid. A second subcutaneous injection of 1.5 mL of the equine-specific composition was performed around the remaining margin of the sarcoid. FIG. 14C shows the sarcoid six months after the subcutaneous injection of the equine-specific composition around the margin of the sarcoid.

Figure 15C:
Figure 15B:
Figure 15A:
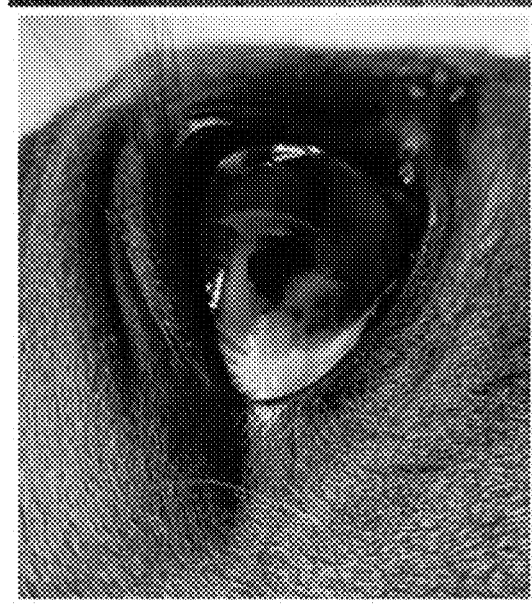

FIGS. 15A, 15B, and 15C show the effects of the finished product (e.g., equine-specific therapeutic composition) on squamous cell carcinoma healing. FIG. 15A shows a squamous cell carcinoma of the eye on the day of subconjunctival injection of 1.5 mL of the equine-specific composition. FIG. 15B shows the squamous cell carcinoma of the eye five weeks after the subconjunctival injection of the equine-specific composition. FIG. 15C shows the squamous cell carcinoma of the eye four months after the subconjunctival injection of the equine-specific composition.

DETAILED DESCRIPTION OF THE INVENTION

For purposes of summarizing the disclosure, certain aspects, advantages, and novel features of the disclosure are described herein. It is to be understood that not necessarily all such advantages may be achieved in accordance with any particular embodiments of the disclosure. Thus, the disclosure may be embodied or carried out in a manner that achieves or optimizes one advantage or group of advantages as taught herein without necessarily achieving other advantages as may be taught or suggested herein.

Additionally, although embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. Moreover, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described herein.

Terms

As used herein, the terms "comprises," "comprising," "includes," "including," "has," "having," or any other variation thereof are intended to cover a non-exclusive inclusion. For example, a process, method, article, or apparatus that comprises a list of elements is not necessarily limited to only those elements but may include other elements not expressly listed or inherent to such process, method, article, or apparatus. Also, the use of "a" or "an" is employed to describe elements and components described herein. This is done merely for convenience and to give a general sense of the scope of the invention. This description should be read to include one or at least one and the singular also includes the plural unless it is obvious that it is meant otherwise.

Placental tissue, as used herein, refers to tissues derived from a placenta, including amnion membrane (i.e., allantoamnion), chorion membrane (i.e., chorioallantois), Wharton's Jelly, umbilical cord, amniotic fluid, allantoic fluid and the like.

As used herein, "allantoamnion," "amnion membrane," "allantoamnion membrane," and "amnion" can be used interchangeably and refer to the inner sac comprising the amniotic fluid and fetus.

As used herein, "chorioallantois," "chorion membrane," "chorioallantois membrane," and "chorion" can be used interchangeably and refer to the outer sac comprising the allantoic fluid.

Micronized placental tissue particles, as used herein, are defined as particles derived from the placenta, including the allantoamnion, the chorioallantois, the umbilical cord, or Wharton's Jelly. Allantoamnion particles may be preferred for therapeutic effectiveness. Placental tissue may be micronized to have an average particle size of about 100 μm in length, width, or thickness and is preferably micronized to have an average particle size of about 10 μm in length, width, or thickness. In some embodiments, the placental tissue may be micronized to have an average particle size of about 2000 μm, or about 1800 μm, or about 1500 μm, or about 1250 μm, or about 1000 μm, or about 900 μm, or about 800 μm, or about 700 μm, or about 600 μm, or about 500 μm, or about 450 μm, or about 400 μm, or about 350 μm, or about 300 μm, or about 250 μm, or about 200 μm, or about 150 μm, or about 100 μm, or about 75 μm, or about 50 μm, or about 25, or about 10 μm, or about 5 μm, or about 1 μm, or about 0.5 μm, or about 0.1 μm and any range between and including the average particle sizes provided. Particle size, average particle size, or particle size distribution may be determined by analysis of scanning electron micrographs or other suitable methods. Micronized placental tissue particles may be formed through any suitable method including, but not limited to, tissue grinding, cryogenic fracturing, application of heat and pressure, sonication, and/or enzyme digestion. The resulting particles may be either used wet, partially dehydrated, or essentially dehydrated by any means known to one of skill in the art, such as, for example, lyophilization.

"Subject," "individual," "animal," and "patient" are used interchangeably herein to refer to mammals, including, but not limited to, rodents, simians, humans, felines, canines, equines, bovines, porcines, ovines, caprines, mammalian laboratory animals, mammalian farm animals, mammalian sport animals, and mammalian pets. In some embodiments, the individual is an equine, dog, cat, pig, cow, camel, or human.

The terms "treating" or "treatment" refer to any indicia of success or amelioration of the progression, severity, and/or duration of an injury, disease, pathology, or condition, including any objective or subjective parameter such as abatement; remission; diminishing of symptoms or making the injury, pathology or condition more tolerable to the patient; slowing in the rate of degeneration or decline; making the final point of degeneration less debilitating; disease modification; or improving a patient's physical or mental well-being.

The terms "manage," "managing," and "management" refer to preventing or slowing the progression, spread, or worsening of an injury, a disease, or disorder or of one or more symptoms thereof. In certain cases, the beneficial effects that a subject derives from a prophylactic or therapeutic agent do not result in a cure for the disease or disorder.

The term "effective amount" as used herein refers to the amount of a pharmaceutical, therapy, or medication that is sufficient to reduce and/or ameliorate the severity and/or duration of a given injury, disease, disorder, or condition and/or a symptom related thereto. This term also encompasses an amount necessary for the reduction or amelioration of the advancement or progression of a given disease (e.g., cancer), disorder or condition, reduction or amelioration of the recurrence, development or onset of a given disease, disorder or condition, and/or to improve or enhance the prophylactic or therapeutic effect(s) of another therapy. In some embodiments, "effective amount," as used herein, also refers to the amount of therapy provided herein to achieve a specified result.

As used herein, and unless otherwise specified, the term "therapeutically effective amount" is an amount sufficient enough to provide a therapeutic benefit in the treatment or management of an injury, a disease or to delay or minimize one or more symptoms associated with the presence of a given disease. A therapeutically effective amount of an agent means an amount of therapeutic agent, alone or in combination with other therapies, which provides a therapeutic benefit in the treatment or management of the injury or disease. The term "therapeutically effective amount" can encompass an amount that improves overall therapy, reduces or avoids symptoms or causes of a given injury, disease, or enhances the therapeutic efficacy of another therapeutic agent.

The terms "administering" and "administration" refer to methods of providing a pharmaceutical, therapy, or medication preparation to a subject. Such methods are well known to those skilled in the art and include, but are not limited to, administering the compositions orally, intranasally, parenterally (e.g., intravenously and subcutaneously), by intramuscular injection, intraarticular injection, intraligamentary injection, intratendon injection, by intraperitoneal injection, subconjunctival injection, intrathecally, transdermally, extracorporeally, topically, inhalation, or the like.

Pharmaceutical compositions for oral administration include, but are not limited to, powders or granules, suspensions or solutions in water or non-aqueous media, pills, lozenges, capsules, sachets, or tablets. Thickeners, flavorings, diluents, emulsifiers, dispersing aids or binders may be desirable. A person of skill, monitoring a subject's clinical response, can adjust the frequency of administration and dosage of the medication according to methods known in the art.

Additionally, the compositions described herein can be administered intranasally or administration by inhalant. As used herein, "intranasal administration" means delivery of the compositions into the nose and nasal passages through one or both of the nares and can comprise delivery by a spraying mechanism (device) or droplet mechanism (device), or through aerosolization of the composition, e.g., by using a nasal spray, atomizer, dropper, or syringe. Administration of the compositions by inhalant can be through the nose or mouth via delivery by a spraying or droplet mechanism. As used herein, "an inhaler" can be a spraying device or a droplet device for delivering the peptide composition, in a pharmaceutically acceptable carrier, to the nasal passages and the upper and/or lower respiratory tracts of a subject. Delivery can also be directly to any area of the respiratory system (e.g., lungs) via intratracheal intubation. A person of skill, monitoring a subject's clinical response, can adjust the frequency of administration and dosage of the medication according to methods known in the art.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, for example, U.S. Pat. No. 3,610,795, which is incorporated by reference herein. In some embodiments, the injectable composition may be administered with saline, antibiotics, blood-derived products, serum, polyacrylamide gel, or other biological products.

In another aspect, the peptide compositions can be administered to a subject intramuscularly, e.g., by using muscular injections or electroporation. A person of skill, monitoring a subject's clinical response, can adjust the frequency of administration and dosage of the medication according to methods known in the art.

As described above, the compositions can be administered to a subject in a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

A "pharmaceutically acceptable carrier" refers to a non-toxic solid, semisolid, or liquid filler, diluent, encapsulating material, formulation auxiliary, or carrier conventional in the art for use with a therapeutic agent for administration to a subject. A pharmaceutically acceptable carrier is non-toxic to recipients at the dosages and concentrations employed, and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

Pharmaceutical compositions can include additional carriers, as well as thickeners, diluents, buffers, preservatives, surface active agents, and the like in addition to the compounds disclosed herein. Pharmaceutical compositions can also include one or more additional active ingredients such as antimicrobial agents, anti-inflammatory agents, anesthetics, and the like. Other suitable pharmaceutically acceptable carriers include solvents, dispersion media, coatings, isotonic and absorption delaying agents, and the like, which are compatible with pharmaceutical administration. Supplementary active compounds can also be incorporated into the compositions.

The terms "decontaminate" or "decontamination," as used herein, may refer to the neutralization and/or killing of all viable microorganisms, as well as the removal or partial removal of all non-viable microorganisms. The process of neutralizing and/or killing viable microorganisms results in the generation of non-viable microorganisms. The terms "decontaminate" and "disinfect" as used herein may be used interchangeably. In some embodiments, equine-specific therapeutic compositions described herein may comprise non-viable microorganisms (e.g., non-viable microorganisms may be cross-linked to the tissue (e.g., the allantoamnion membrane).

The term "protein" as used herein can be the full-length polypeptide, or a fragment or segment of a polypeptide, and can encompass a stretch of amino acids residues of at least about 8 amino acids, generally at least 10 amino acids, more generally at least 20 amino acids, often at least 30 amino acids, more often at least 50 amino acids or more of the full-length polypeptide.

The term "exosomes" refers to extracellular vesicles released from cells and containing proteins, lipids, mRNA, miRNA, and DNA.

The term "biocomponent," as used herein, may refer to any component having a biological origin and may include proteins, carbohydrates, exosomes, lipids, nucleic acids, microorganisms (e.g., bacteria) and their derivatives, postbiotics, or a combination thereof.

The term "postbiotic," as used herein, refers to any substance released by or produced through the metabolic activity of microorganisms and/or fragments of microorganisms, which exerts a beneficial effect on the host, directly or indirectly. In some embodiments, postbiotics do not contain viable microorganisms. In some embodiments, postbiotics comprise non-viable microorganisms and derivatives thereof. In some embodiments, postbiotics include cell-free supernatants that contain biologically active metabolites secreted by bacteria and yeast into the surrounding liquid/environment. In some embodiments, postbiotics include biopolymers released outside the cell wall (bacterial, yeast, or cells) cell wall, forming a heterogeneous group of substances called exopolysaccharides (EPSs). In some embodiments, postbiotics include antioxidant enzymes, such as glutathione peroxidase (GPx), peroxide dismutase (SOD), catalase, and NADH-oxidase that play key roles in combating reactive oxygen species (ROS), which can damage lipids, proteins, carbohydrates, and nucleic acids. In some embodiments, postbiotics include bacterial cell walls, including bacterial lipoteichoic acid (LTA), that elicit a specific immune response. LTA is found in the cell walls of Gram-positive bacteria. In some embodiments, postbiotics include short-chain fatty acids that are products of fermentation of polysaccharides by intestinal microbiota. In some embodiments, postbiotics include bacterial lysates (BLs) that are obtained by the chemical or mechanical degradation of Gram-positive and Gram-negative bacteria. BLs mimic the presence of bacteria and stimulate the immune system.

Referring now to FIG. 1-15C, the present invention features methods for processing equine placental tissues into a clear, safe, and physiologically and biologically active liquid product that may be delivered via injection or any other therapeutically appropriate route of administration. Additionally, the present invention features methods for treating equine ailments using the equine-specific therapeutic composition produced and described here.

Equine-Specific Therapeutic Compositions

The present invention features an equine-specific therapeutic composition. The equine-specific therapeutic composition may comprise placental tissue (e.g., equine-specific placental tissue) and a carrier solution. The placental tissue (e.g., equine-specific placental tissue) comprises an allantoamnion membrane, a chorioallantois membrane, an umbilical cord, Wharton's Jelly, an amniotic fluid, an allantoic fluid, or a combination thereof. The allantoamnion membrane comprises amniotic fluid and the chorioallantois membrane comprises allantoic fluid. Other placental tissue may be used in accordance with the methods and compositions as described herein. In some embodiments, the composition is derived or made from placental tissue or fluid from a human, horse, canine, feline, porcine, bovine, camel, or the like.

As used herein, a "carrier solution" or a "working solution" may be used interchangeably and refers to a solution comprising processed amniotic fluid. The carrier solution may further comprise an isotonic solution. Non-limiting examples of isotonic solutions include but are not limited to Plasma Lyte A, NaCl solution, a phosphate buffer, or the like. In some embodiments, a carrier solution comprises processed amniotic fluid and an isotonic solution. In some embodiments, the carrier solution may further comprise hypertonic solutions, DMEM, water, or a combination thereof. In certain embodiments, the carrier solution may further comprise a cryopreservative, a stabilizer, buffers, collagen, hyaluronic acid, antimicrobial agents such as antibiotics or antifungal agents, surfactants, pH modifiers, synthetic polymers, proteins, postbiotics, exosomes, amniotic fluid, allantoic fluid or a combination thereof.

Alternatively, the equine-specific therapeutic composition may comprise an allantoamnion membrane (e.g., an equine-specific allantoamnion membrane) and a carrier solution. In some embodiments, the carrier solution comprises amniotic fluid (e.g., equine-specific amniotic fluid). The carrier solution may further comprise proteins, exosomes, and postbiotics derived from the amniotic fluid (e.g., amniotic fluid specific proteins and postbiotics). The allantoamnion membrane (e.g., an equine-specific allantoamnion membrane) may comprise proteins, exosomes, and postbiotics derived from said membrane (e.g., allantoamnion-specific proteins and postbiotics). In some embodiments, the allantoamnion membrane comprises allantoamnion membrane particles (e.g., micronized allantoamnion membrane particles).

In some embodiments, the equine-specific therapeutic composition comprises an allantoamnion membrane (e.g., an equine-specific allantoamnion membrane), amniotic fluid (e.g., an equine-specific amniotic fluid), a carrier solution, or a combination thereof. For example, the equine-specific therapeutic composition may comprise an allantoamnion membrane and amniotic fluid or an allantoamnion membrane, amniotic fluid, and a carrier solution. In some embodiments, the allantoamnion membrane is an equine-specific allantoamnion membrane. In some embodiments, the amniotic fluid is an equine-specific amniotic fluid. In some embodiments, the allantoamnion membrane comprises allantoamnion particles.

In some embodiments, the equine-specific therapeutic composition comprises a chorioallantois membrane and a carrier solution. In other embodiments, the equine-specific therapeutic composition comprises a chorioallantois membrane, allantoic fluid, a carrier solution, or a combination thereof. In some embodiments, the chorioallantois membrane is an equine-specific chorioallantois membrane. In some embodiments, the allantoic fluid is an equine-specific allantoic fluid.

In certain embodiments, the equine-specific therapeutic composition comprises an allantoamnion membrane, a chorioallantois membrane, an amniotic fluid, an allantoic fluid, an umbilical cord, Wharton's Jelly, a carrier solution, or a combination thereof. Non-limiting examples of the equine-specific therapeutic composition described herein are shown in Table 1.

Table 1 (below) shows non-limiting examples of equine-specific therapeutic compositions described herein.

| | allantoamnion membrane | chorioallantois membrane | amniotic fluid | allantoic fluid | umbilical cord | Wharton's Jelly | Carrier Fluid |
|---|---|---|---|---|---|---|---|
| Composition A | ✓ | | | | | | ✓ |
| Composition B | ✓ | | ✓ | | | | ✓ |
| Composition C | ✓ | | | | ✓ | | ✓ |
| Composition D | ✓ | | ✓ | | ✓ | | ✓ |
| Composition E | ✓ | | | | | ✓ | ✓ |
| Composition F | ✓ | | ✓ | | | ✓ | ✓ |
| Composition G | ✓ | | | | ✓ | ✓ | ✓ |

-continued

| | allanto-amnion membrane | chorioal-lantois membrane | amniotic fluid | allantoic fluid | umbilical cord | Wharton's Jelly | Carrier Fluid |
|---|---|---|---|---|---|---|---|
| Composition H | ✓ | | ✓ | | ✓ | ✓ | ✓ |
| Composition I | | ✓ | | | | | ✓ |
| Composition J | | ✓ | | ✓ | | | ✓ |
| Composition K | | ✓ | | | ✓ | | ✓ |
| Composition L | | ✓ | | ✓ | ✓ | | ✓ |
| Composition M | | ✓ | | | | ✓ | ✓ |
| Composition N | | ✓ | | ✓ | | ✓ | ✓ |
| Composition O | | ✓ | | | ✓ | ✓ | ✓ |
| Composition P | | ✓ | | ✓ | ✓ | ✓ | ✓ |
| Composition Q | ✓ | ✓ | | | | | ✓ |
| Composition R | ✓ | ✓ | ✓ | | | | ✓ |
| Composition S | ✓ | ✓ | | ✓ | | | ✓ |
| Composition T | ✓ | ✓ | | | ✓ | | ✓ |
| Composition U | ✓ | ✓ | ✓ | | ✓ | | ✓ |
| Composition V | ✓ | ✓ | | ✓ | ✓ | | ✓ |
| Composition W | ✓ | ✓ | | | | ✓ | ✓ |
| Composition X | ✓ | ✓ | ✓ | | | ✓ | ✓ |
| Composition Y | ✓ | ✓ | | ✓ | | ✓ | ✓ |
| Composition Z | ✓ | ✓ | | | ✓ | ✓ | ✓ |
| Composition AA | ✓ | ✓ | ✓ | | ✓ | ✓ | ✓ |
| Composition BB | ✓ | ✓ | | ✓ | ✓ | ✓ | ✓ |
| Composition CC | ✓ | ✓ | ✓ | ✓ | ✓ | ✓ | ✓ |

In some embodiments, equine-specific therapeutic composition described herein further comprise allantoamnion membrane particles, chorioallantois membrane particles, umbilical cord, Wharton's Jelly or a combination thereof. In other embodiments, the compositions described herein further comprise amniotic fluid, allantoic fluid, or a combination thereof. In other embodiments, the compositions described herein further comprise cells from the amniotic fluid, allantoic fluid, or a combination thereof.

In some embodiments, the aforementioned equine-specific therapeutic compositions are acellular. An acellular composition, as used herein, is defined as a composition having essentially no viable cells or no more than 1% of the total number of cells in the material are viable. In an exemplary embodiment, an acellular composition contains no viable cells. In an exemplary embodiment, an acellular composition is essentially cell free. Essentially cell free, as used herein, is defined as a composition that contains essentially no cells, wherein the cells have been removed or destroyed through cryo-fracturing, for example. Thus, in some embodiments, the equine-specific therapeutic composition may comprise an acellular allantoamnion membrane (e.g., acellular allantoamnion membrane particles) and a carrier solution (e.g., comprising an acellular amniotic fluid) . In other embodiments, the equine-specific therapeutic composition may comprise an allantoamnion membrane (e.g., allantoamnion membrane particles) and a carrier solution (e.g., comprising an acellular amniotic fluid), wherein the allantoamnion membrane (e.g., allantoamnion membrane particles) comprise non-viable cells. Alternatively, in certain embodiments, the equine-specific therapeutic compositions described herein composition may comprise live or viable cells.

In some embodiments, the compositions described herein further comprise one or more of: proteins, postbiotics, growth factors, cytokines, peptides, lipids, exosomes, mRNA, and/or miRNA from the amniotic fluid, allantoic fluid, or a combination thereof. In some embodiments, the compositions described herein further comprise one or more of: proteins, postbiotics, growth factors, cytokines, peptides, lipids, exosomes, mRNA, and miRNA from allantoamnion membrane particles, chorioallantois membrane particles, umbilical cord, Wharton's Jelly or a combination thereof. In other embodiments, the compositions described herein comprise one or more of: proteins, postbiotics, growth factors, cytokines, peptides, lipids, exosomes, mRNA, and miRNA from the amniotic fluid, allantoic fluid or a combination thereof mixed with one or more of: proteins, postbiotics, growth factors, cytokines, peptides, lipids, exosomes, mRNA, and miRNA from allantoamnion membrane particles, chorioallantois membrane particles, umbilical cord, Wharton's Jelly or a combination thereof to create a unique equine-specific therapeutic composition.

In some embodiments, the compositions described herein comprise proteins. In some embodiments, the compositions described herein comprise exosomes. In some embodiments, the proteins have anti-inflammatory properties, anti-fibrotic properties, anti-microbial properties, anti-atherosclerotic properties, autophagy, healing properties, repairing properties, immunoregulatory properties, anti-cancer properties, or a combination thereof. Proteins, e.g., within the composition, may include but are not limited to IL1-ra, IL-1a, IL-1b, IL-2, IL-4, IL-6, IL-8, IL-10, MCP-1, VEGF, TIMP-1, TIMP-2, TIMP-3, TIMP-4, IGF, EGF, FGF, TGFb1, alpha-2-microglobulin, hyaluronic acid, proteoglycans, collagen, fibronectin, laminin and the like. In some embodiments, the exosomes have anti-inflammatory properties, immunomodulatory properties, tissue repair, and regeneration properties.

In some embodiments, the postbiotics comprise metabolites and fragments of non-viable microorganisms and/or their derivatives. Without wishing to limit the present invention to any theory or mechanism, it is believed that non-viable microorganisms or their derivatives within the composition may help elicit a desirable immune response (e.g., healing and antitumor properties). Thus, in some embodiments, the compositions described herein may elicit an immune response, e.g., a desirable immune response, e.g., a beneficial activation of the immune system. Postbiotics may have anti-inflammatory properties, anti-fibrotic properties, anti-microbial properties, anti-atherosclerotic properties, autophagy, healing properties, repairing properties, immunoregulatory properties, anti-cancer properties, or a combination thereof. In other embodiments, the postbiotics may comprise metabolites of non-viable or viable microorganisms or their derivatives, or fragments of non-viable or viable microorganisms or their derivatives, or combinations thereof.

The equine-specific therapeutic compositions described herein may further comprise cell-free supernatants, biopolymers (e.g., exopolysaccharides), enzymes (e.g., antioxidant enzymes such as glutathione peroxidase, peroxide dismutase, catalase, and NADH-oxidase), cell wall fragments (e.g., lipoteichoic acid), short-chain fatty acids (e.g., acetate, propionate, butyrate), bacterial lysates, or a combination thereof.

In some embodiments, the compositions described herein are clear, safe, and physiologically and biologically active.

In some embodiments, compositions described herein are free or substantially free of contaminants. As used herein, 'contaminant' refers to any potentially harmful substance, including viable microorganisms or any other agents capable of causing infection, undesirable immune responses, or illness. Contaminants encompass substances that may compromise the integrity or desired properties of the compositions described herein, such as bacteria, viruses, fungi, toxins, and blood-related components, including blood vessels.

Non-limiting examples of contaminants may include but are not limited to, blood-related components (e.g., plasma, red blood cells, white blood cells, platelets, wastes), immunogenic blood-related components, microorganisms (e.g., bacteria, e.g., aerobic bacteria or anaerobic bacteria, or viruses), fungi (e.g., yeast) or a combination thereof. The contaminants may further include byproducts of hemoglobin metabolism and/or catabolism, e.g., iron, heme, globin, biliverdin, bilirubin, or alternatively include products of hemoglobin breakdown. In some embodiments, the contaminants are immunogenic. Without wishing to limit the present invention to any theory or mechanism, it is believed that the removal of contaminants mitigates the risk of an equine recipient having an immunogenic response towards the composition, thereby improving equine recipient safety and increasing the effectiveness of the compositions by preventing graft rejection.

In some embodiments, compositions described herein do not elicit an immune-mediated reaction (e.g., an undesirable immune-mediated reaction) upon administration to an individual (e.g., an equine allograft recipient). In some embodiments, compositions described herein do not elicit a clinically significant immune-mediated reaction upon (e.g., an undesirable immune-mediated reaction) administration to an equine allograft recipient. In some embodiments, compositions described herein do not elicit an alloimmunization response upon administration to an equine allograft recipient. In some embodiments, compositions described herein do not elicit a clinically significant alloimmunization response upon administration to an equine allograft recipient. Without wishing to limit the present invention to any theory or mechanism, it is believed that these properties of the present invention mitigate the risk of an equine patient having an immunogenic and/or alloimmunization response towards the composition, thereby improving equine-patient recipient safety and increasing the effectiveness of the compositions by preventing graft rejection.

Rather, in some embodiments, the equine-specific therapeutic compositions described herein may elicit a desired immune response upon administration to an individual (e.g., an equine allograft recipient). For example, without wishing to limit the present invention to any theory or mechanism, it is believed that non-viable microorganisms or their derivatives (e.g., postbiotics) could induce a beneficial activation of the immune system, potentially resulting in mild and transient effects such as swelling, pain, redness, or a combination thereof.

As used herein, an "undesirable immune response" refers to hypersensitivity to the equine-specific therapeutic compositions, e.g., severe pain, severe swelling, severe redness, or infection. Alternatively, as used herein, a "desirable immune response" refers to mild and transient swelling, pain, redness, and beneficial activation of the immune system.

The allantoamnion comprises three layers. In some embodiments, the three layers of the allantoamnion comprise a first layer, a second layer, and a third layer. The first and third layers comprise an epithelial layer and a basement membrane layer, and the second layer comprises a mesenchymal (i.e., stromal) layer. In some embodiments, all three layers of the allantoamnion are utilized in the compositions described herein. In some embodiments, the first layer, the second layer, the third layer, or a combination thereof are utilized in the composition described herein. The mesenchymal layer is a matrix and may comprise blood vessels. In some embodiments, the blood vessels are removed from the mesenchymal layer. The blood vessels may be removed from the mesenchymal layer with forceps, e.g., forceps may be used to pluck the blood vessels out of the mesenchymal layer. In other embodiments, the blood vessels are removed from the mesenchymal layer by separating the two epithelial and basal layers and removing (i.e., peeling off) the blood vessels. In some embodiments, the two epithelial and basal layers are put back together. Non-limiting examples of how blood vessels may be removed include scraping, peeling, rinsing, blunt dissection, or the like; however, the present invention is not limited to these methods.

In some embodiments, compositions described herein are free of blood vessels. In other embodiments, the compositions described herein are mostly free of blood vessels. In further embodiments, the compositions described herein comprise blood vessels. Without wishing to limit the present invention to any theory or mechanism, it is believed that the removal of the blood vessels mitigates the risk of an equine patient having an immunogenic response towards the composition.

In some embodiments, compositions described herein are liquids or suspensions substantially free of contaminants. For example, the compositions described herein are liquids or suspensions substantially free of microorganisms (e.g., viable microorganisms). Alternatively, the compositions described herein are liquids or suspensions substantially free of viable microorganisms but may comprise non-viable microorganisms (e.g., postbiotics). In some embodiments, the compositions described herein are liquids or suspensions comprising non-viable microorganisms.

In some embodiments, the compositions are a substantially colorless liquid or suspension. In some embodiments, the compositions are substantially clear liquids or suspensions. In some embodiments, the compositions are substantially clear and colorless liquids or suspensions. In some embodiments, the compositions are substantially cloudy and colorless liquids or suspensions. One of ordinary skill in the art would readily understand the intended meaning of the terms clear, cloudy, or colorless with regard to the visual appearance of the composition described herein.

Without wishing to limit the present invention to any theory or mechanism, it is believed that the aforementioned properties of the present invention represent the removal of contaminants from the compositions described herein, thus mitigating the risk of an equine recipient having an immunogenic and/or alloimmunization response towards the composition, thereby improving equine patient-recipient safety and increasing the effectiveness of the compositions by preventing graft rejection.

In some embodiments, the compositions comprise about 1 $cm^2$ of allantoamnion membrane per about 1 mL of working solution. In other embodiments, the compositions comprise about 2 $cm^2$ of allantoamnion membrane per about 1 mL of working solution. Without wishing to limit the present invention to any theory or mechanism, it is believed that these ratios may produce fewer adverse effects and achieve superior therapeutic results compared to other ratios. In specific embodiments, the composition ratios may vary depending on factors such as the tissue utilized in its creation and the quantity of proteins, exosomes, and/or postbiotics present in that tissue. The determination of ratios may be guided by the protein, exosomes, and/or postbiotics content inherent in the composition.

In some embodiments, the equine-specific therapeutic composition comprises about 5 $cm^2$ of allantoamnion membrane, or about 10 $cm^2$ of allantoamnion membrane, or about 25 $cm^2$ of allantoamnion membrane, or about 50 $cm^2$ of allantoamnion membrane, or about 75 $cm^2$ of allantoamnion membrane, or about 100 $cm^2$ of allantoamnion membrane per about 1 mL of working solution (e.g., carrier solution).

In some embodiments, the compositions described herein are injectable. In other embodiments, the compositions described herein are for topical use. In other embodiments, the compositions described herein may be applied intravenously or intra-arterially. In other embodiments, the compositions described herein may be applied by inhalation. In other embodiments, the compositions described herein may be used intraoperatively. In other embodiments, the compositions described herein may be used postoperatively. In other embodiments, the compositions described herein may be in the form of a liquid or gel, hydrogel, ointment, polymer, cream, lotion, foam, oil, paste, capsule, lyophilized, dehydrated, or tablet.

The therapeutic compositions described herein may be made from placental tissue and/or fluid from any suitable mammalian donor, including humans, horses, canines, felines, pigs, and the like. In addition, the therapeutic compositions may be used to treat a treatment location of any suitable mammalian patient, including a horse, dog, cat, or human, for example.

Methods of Use Thereof

The present invention may also feature a method of treating cancer in an individual (e.g., an equine). The method may comprise administering a therapeutic amount of a composition as described herein, to the individual (e.g., the equine) in need thereof. In other embodiments, the present invention features a method of preventing cancer in an individual (e.g., an equine). In some embodiments, the method comprises administering a therapeutic amount of a composition, as described herein, to the individual (e.g., the equine) in need thereof. Exemplary cancers that may be treated with the compositions described herein include but are not limited to, melanomas, squamous cell carcinomas, and sarcoids. In non-limiting embodiments, the individual is an equine, dog, cat, pig, cow, camel, or human.

In some embodiments, the equine-specific therapeutic compositions described herein are used as regenerative products. In other embodiments, the equine-specific therapeutic compositions described herein are a biodegradable and/or bioabsorbable tissue scaffold. Without wishing to limit the present invention to any theory or mechanism, it is believed that after the equine-specific therapeutic composition is injected into a target site, proteins, cellular excretions, cellular derivatives, and extracellular matrix components from the composition will elute out/be absorbed into the native surrounding tissue. Also, the membrane particles may act as a scaffold to facilitate migration of the surrounding cells, reinforce adhesion of the basal epithelium, promote cellular differentiation, and prevent apoptosis.

In some embodiments, compositions described herein may be used to treat various equine ailments. Non-limiting examples of equine ailments that may be treated with compositions described herein include but are not limited to cancer, benign tumors, joint diseases, soft tissue lesions, inflammatory diseases, immunological diseases, neurological diseases, skin wounds and repair (e.g., burns, necrosis, scarring, skin ulcers and venous ulcers), ocular wounds and repair (e.g., glaucoma, ocular ulcers, corneal ulcers, conjunctival scleral and lid and orbital rim reconstruction), coronary wounds and repair (e.g. coronary bypass, heart valve repair and replacement, vein repair and artery repair), nerve injuries, spinal injuries, muscle tears, organ diseases, among others. In other embodiments, compositions described herein may have anticancer effects. In other embodiments, compositions described herein may have immunoregulatory effects.

The present invention may further feature a method of treating or preventing cancer in an equine. In some embodiments, the method comprises administering a therapeutic amount of equine-specific therapeutic composition comprising placental tissue and a working solution.

Methods of Producing

The present invention features methods of producing equine-specific therapeutic compositions described herein. The method may comprise obtaining equine placental tissue and amniotic fluid and processing the equine placental tissue and amniotic fluid. In some embodiments, the equine placental tissue and amniotic fluid may be processed simultaneously. In other embodiments, the equine placental tissue and amniotic fluid may be processed asynchronously. In some embodiments, processing the equine placental tissue produces micronized placental tissue particles free of contaminants and containing a concentration of placental tissue-derived biocomponents (e.g., proteins, exosomes, and postbiotics). In some embodiments, processing the equine amniotic fluid produces an amniotic fluid solution free of cells and contaminants and containing a concentration of amniotic fluid-derived biocomponents (e.g., proteins, exosomes, and postbiotics). The method further comprises mixing the equine placental tissue micronized particles and the amniotic fluid solution to provide an equine-specific therapeutic composition. In some embodiments, the method may further comprise cryofreezing the equine-specific therapeutic composition.

In some embodiments, processing the placental tissue comprises rinsing, decontaminating, or rinsing and decontaminating the placental tissue. Additionally, processing the placental tissue may further comprise drying the allantoamnion membrane. In some embodiments, processing the placental may further comprise micronzing the placental tissue (e.g., into placental tissue particles). The micronized placental tissue may be then resuspended into a carrier solution (e.g., a carrier solution comprising amniotic fluid) to create the equine-specific therapeutic composition. In some embodiments, the micronized placental tissue particles are resuspended into the processed amniotic fluid to create an equine-specific therapeutic composition. In other embodiments, the micronized placental tissue particles are resuspended into the processed amniotic fluid and a carrier solution to create an equine-specific therapeutic composition.

In some embodiments, the method comprises obtaining an equine allantoamnion membrane and amniotic fluid and processing the equine allantoamnion membrane and amniotic fluid. In some embodiments, the equine allantoamnion membrane and amniotic fluid may be processed simultaneously. In other embodiments, the equine allantoamnion membrane and amniotic fluid may be processed asynchronously. In some embodiments, processing the equine allantoamnion membrane produces micronized allantoamnion membrane particles free of contaminants and containing a concentration of placental tissue-derived biocomponents (e.g., proteins, exosomes, and postbiotics). In some embodiments, processing the equine amniotic fluid produces an amniotic fluid solution free of cells and contaminants and containing a concentration of amniotic fluid-derived biocomponents (e.g., proteins, exosomes, and postbiotics). The method further comprises mixing the allantoamnion membrane micronized particles and the amniotic fluid solution to provide an equine-specific therapeutic composition. In some embodiments, the method may further comprise cryofreezing the equine-specific therapeutic composition.

In some embodiments, processing the allantoamnion membrane comprises rinsing, decontaminating, or rinsing and decontaminating allantoamnion membrane. Additionally, processing the allantoamnion membrane may further comprise drying the allantoamnion membrane. In some embodiments, processing the allantoamnion membrane may further comprise micronizing the allantoamnion membrane (e.g., into allantoamnion membrane particles). The micronized allantoamnion membrane particles may be then resuspended into a carrier solution (e.g., a carrier solution comprising amniotic fluid) to create the equine-specific therapeutic composition. In some embodiments, the micronized allantoamnion membrane particles are resuspended into the processed amniotic fluid to create an equine-specific therapeutic composition. In other embodiments, the micronized allantoamnion membrane particles are resuspended into the processed amniotic fluid and a carrier solution to create an equine-specific therapeutic composition.

The allantoamnion membrane may be processed such that at least one layer of the allantoamnion membrane is retained. In other embodiments, the allantoamnion membrane may be processed such that at least two layers of the allantoamnion membrane are retained. The allantoamnion membrane may be processed such that all layers of the allantoamnion membrane are retained.

The tissues (e.g., placental tissue or allantoamnion membrane) used herein may be decontaminated prior to or after the micronizing process. Without wishing to limit the present invention to any theory or mechanism, it is believed that the decontamination process described herein allows for the elimination of viable contaminants without necessarily removing the non-viable microorganisms and their derivatives from the tissue (e.g., placental tissue or allantoamnion tissue).

In some embodiments, decontaminating the tissue (e.g., placental tissue or allantoamnion membrane) comprises removing the blood vessels and/or other contaminants. The allantoamnion membrane may be rinsed to remove blood vessels and other contaminants. The allantoamnion membrane may be sequentially rinsed to remove blood, blood vessels, and other contaminants. The allantoamnion membrane may be dissected to remove the blood vessels and/or other contaminants. In one aspect, decontaminating the tissue may comprise utilizing a premixed antibiotic solution comprising a cocktail of antibiotics such as gentamicin, ciprofloxacin, streptomycin, or a combination thereof. In some embodiments, the premixed antibiotic solution may be added and mixed with the tissue (e.g., placental tissue or allantoamnion membrane). In another aspect, decontaminating the tissue may comprise utilizing a solution comprising one or more of: 0.1-10% Triton-X, alcohol, ethyl alcohol, isopropyl alcohol, bleach, hydrogen peroxide, surfactants (anionic, cationic, and nonionic), chemical decontaminants such as oxidizing agents (hydrochlorite, sodium hypochlorite, strong bases (calcium oxide, sodium hydroxide) and microemulsions (calcium hydrochlorite, sodium hydroxide).

In other aspects, decontaminating the tissue (e.g., placental tissue or allantoamnion membrane) may comprise exposing the tissue to ultraviolet UV radiation. In other aspects, decontaminating the tissue (e.g., placental tissue or allantoamnion membrane) may comprise exposing the tissue to e-beam radiation, ethylene oxide, or gamma radiation.

In some embodiments, processing the amniotic fluid may comprise centrifuging the amniotic fluid, decontaminating the amniotic fluid, and filtering the amniotic fluid. In some embodiments, processing the amniotic fluid comprises decontaminating the amniotic fluid. In some embodiments, decontaminating the amniotic fluid may comprise centrifugation, serial filtration with specific micron-size filters, or a combination thereof. In other embodiments, decontaminating the amniotic fluid may comprise filtering the amniotic fluid through a mesh filter, centrifugation, serial filtration with specific micron-size filters, or a combination thereof. In further embodiments, decontaminating the amniotic fluid may comprise exposing the amniotic fluid to ultraviolet (UV) radiation. In other aspects, decontaminating the amniotic fluid may comprise exposing the fluid to e-beam or gamma radiation.

In some embodiments, processing the amniotic fluid produces an acellular amniotic fluid. In other embodiments, processing the amniotic fluid produces an amniotic fluid comprising non-viable cells. In certain embodiments, processing the amniotic fluid produces an amniotic fluid comprising cells (e.g., non-viable cells) and other contaminants. Alternatively, in certain embodiments, processing the amniotic fluid produces an amniotic fluid that may comprise live or viable cells.

In certain embodiments, the final product (e.g., equine-specific therapeutic composition) may undergo decontamination and/or sterilization. For example, the equine-specific therapeutic composition may be exposed to ultraviolet (UV) radiation, e-beam, ethylene oxide, or gamma radiation.

The methods described herein may further comprise lyophilization of the equine-specific therapeutic composition. Alternatively, the tissue (e.g., placental tissue or allantoamnion membrane) or the fluid (such as amniotic fluid) may undergo lyophilization individually or in combination before being mixed to form the equine-specific therapeutic composition outlined in this description. For example, in some embodiments, the processed tissue (e.g., placental tissue or allantoamnion membrane) may be lyophilized. In other embodiments, the micronized tissue particles (e.g., the micronized placental tissue particles or the micronized allantoamnion membrane particles) may be lyophilized. In further embodiments, the fluid (e.g., the processed fluid; e.g., the process amniotic fluid) may be lyophilized. In certain embodiments, both the tissue and the fluid are lyophilized.

In some embodiments, the tissue (e.g., placental tissue or allantoamnion membrane) can be frozen prior to the micronizing process. The freezing step can occur by any suitable cooling process. For example, the tissue can be flash-frozen using liquid nitrogen. Alternatively, the material can be placed in an isopropanol/dry ice bath or can be flash-frozen in other coolants. Additionally, the material can be placed in a freezer and allowed to equilibrate to the storage temperature more slowly rather than being flash-frozen. The tissue can be stored at any desired temperature. For example, −20° C. or −80° C. or other temperatures can be used for storage. In other embodiments, the methods described herein further comprise storing the equine-specific therapeutic composition at room temperature. In some embodiments, the methods described herein further comprise storing the equine-specific therapeutic composition at refrigerator temperature. In further embodiments, the methods described herein further comprise storing the equine-specific therapeutic composition below 0° C. (e.g., −20° C., −80° C., or −196° C.).

In some embodiments, the equine-specific therapeutic composition may be stored at or below 25° C. (e.g., about room temperature). For example, the equine-specific therapeutic composition may be stored at about 10° C. to 25° C., or about 10° C. to 20° C., or about 10° C. to 15° C., or about 15° C. to 25° C., or about 15° C. to 20° C., or about 20° C. to 25° C. In some embodiments, the equine-specific therapeutic composition may be stored at about 25° C. In some embodiments, the equine-specific therapeutic composition may be stored at about 20° C. In some embodiments, the equine-specific therapeutic composition may be stored at about 15° C. In some embodiments, the equine-specific therapeutic composition may be stored at about 10° C.

In other embodiments, the equine-specific therapeutic composition may be stored at or below about 5° C. For example, the equine-specific therapeutic composition may be stored at about 0° C. to 5° C., or about 0° C. to 4° C., or about 0° C. to 3° C., or about 0° C. to 2° C., or about 0° C. to 1° C., or about 1° C. to 5° C., or about 1° C. to 4° C., or about 1° C. to 3° C., or about 1° C. to 2° C., or about 2° C. to 5° C., or about 2° C. to 4° C., or about 2° C. to 3° C., about 3° C. to 5° C., or about 3° C. to 4° C., or about 4° C. to 5° C. In some embodiments, the equine-specific therapeutic composition may be stored at about 5° C. In some embodiments, the equine-specific therapeutic composition may be stored at about 4° C. In some embodiments, the equine-specific therapeutic composition may be stored at about 3° C. In some embodiments, the equine-specific therapeutic composition may be stored at about 2° C. In some embodiments, the equine-specific therapeutic composition may be stored at about 1° C.

In some embodiments, the equine-specific therapeutic composition may be stored at or below 0° C. (e.g., freezing temperature). For example, the equine-specific therapeutic composition may be stored at about −196° C. to 0° C., or about −196° C. to −20° C., or about −196° C. to −80° C., or about −80° C. to 0° C., or about −80° C. to −20° C., or about −20° C. to 0° C. In some embodiments, the equine-specific therapeutic composition may be stored at about −196° C. In some embodiments, the equine-specific therapeutic composition may be stored at about −80° C. In some embodiments, the equine-specific therapeutic composition may be stored at about −20° C. In some embodiments, the equine-specific therapeutic composition may be stored at about 0° C.

In other embodiments, the method comprises obtaining an equine-specific allantoamnion membrane and equine-specific amniotic fluid and processing the equine-specific allantoamnion membrane and equine-specific amniotic fluid. The method may further comprise rinsing and/or decontaminating the allantoamnion membrane and decontaminating the amniotic fluid. In some embodiments, the method comprises micronizing said allantoamnion membrane (e.g., to form allantoamnion membrane particles). In some embodiments, obtaining an allantoamnion membrane comprises obtaining a whole equine placenta and dissecting the whole equine placenta to obtain the allantoamnion membrane. In some embodiments, the methods described herein further comprise processing the allantoamnion membrane to retain all layers of the allantoamnion membrane. In other embodiments, the methods described herein further comprise processing the allantoamnion membrane to retain one or more layers of the allantoamnion membrane. In further embodiments, the methods described herein further comprise processing the allantoamnion membrane to retain two or more layers of the allantoamnion membrane.

In some embodiments, processing the allantoamnion membrane further comprises removing the blood vessels. In some embodiments, the methods described herein further comprise rinsing to remove blood or contaminants and drying the allantoamnion membrane. In other embodiments, the methods described herein further comprise cryofracturing the allantoamnion membrane to produce allantoamnion particles. In other embodiments, the methods described herein further comprise resuspending the allantoamnion particles in a working solution to produce an equine-specific therapeutic composition. In other embodiments, the methods described herein further comprise freezing the equine-specific therapeutic composition. In some embodiments, freezing the equine-specific therapeutic composition preserves proteins.

The present invention may further feature a method of producing an equine-specific therapeutic composition. In some embodiments, the method comprises obtaining a whole equine placenta. In some embodiments, the method comprises dissecting the whole equine placenta and retaining an allantoamnion membrane. In some embodiments, the method comprises rinsing the allantoamnion membrane, decontaminating the allantoamnion membrane, and drying the allantoamnion membrane. In some embodiments, the method comprises micronizing the aforementioned allantoamnion membrane and resuspending the micronized allantoamnion membrane into a working solution to create an equine-specific therapeutic composition. In other embodiments, the method further comprises freezing the equine-specific therapeutic composition to preserve proteins.

In some embodiments, the whole equine placenta is obtained after a live birth. In other embodiments, the whole equine placenta is obtained after a scheduled c-section.

In some embodiments, the equine placental tissue is transported without a transport solution (i.e., a saline solution). In some embodiments, the equine placental tissue is transported wet. In other embodiments, the equine placental tissue is transported wet in a jar. In further embodiments, the allantoamnion is separated from the equine placenta, placed into a jar, and then transported. Without wishing to limit the present invention to any theories or mechanisms, it is believed that transporting the equine placental tissue with a transport solution (e.g., saline solution) advantageously provides for an increase in retained proteins within the placenta as compared to an equine placenta transported in a without transport solution. When transported in a transport solution (e.g., a saline solution), proteins (~40%) elute out of the placental membranes and into the transport solution. However, in certain embodiments, the equine placental tissue is transported in a transport solution (i.e., a saline solution).

In some embodiments, the amniotic fluid is transported in a container, e.g., a bottle or a jar.

In some embodiments, the method further comprises processing the allantoamnion membrane to retain all three layers of the allantoamnion membrane. In some embodiments, the blood vessels are removed from the allantoamnion membrane. In some embodiments, the allantoamnion membrane further comprises amniotic fluid.

In certain embodiments, the allantoamnion membrane is rinsed once. In some embodiments, the allantoamnion membrane is rinsed twice. In other embodiments, the allantoamnion membrane is rinsed three times, four times, or five times.

In certain embodiments, the allantoamnion membrane may be rinsed for 10 seconds. In other embodiments, the allantoamnion membrane may be rinsed for about 1 minute, or about 2 minutes, or about 5 minutes, or about 10 minutes, or about 15 minutes, or about 20 minutes, or about 25 minutes, or about 30 minutes, or about 35 minutes, or about 40 minutes, or about 45 minutes, or about 50 minutes, or about 55 minutes, or about 60 minutes, or about 65 minutes, or about 70 minutes, or about 75 minutes, or about 80 minutes, or about 85 minutes, or about 90 minutes, or about 180 minutes. Without wishing to limit the present invention to any theory or mechanism, it is believed that gently rinsing the allantoamnion membrane (instead of washing) allows for the retention of biocomponents. In accordance with the methods described herein, the allantoamnion membrane may be rinsed using any appropriate solution, including but not limited to a buffer solution, with or without antibiotics.

In certain embodiments, the allantoamnion membrane is decontaminated for about 10 seconds, or about 30 seconds, or about 45 seconds, or about 1 minute, or about 2 minutes, or about 5 minutes, or about 10 minutes, or about 15 minutes, or about 20 minutes, or about 25 minutes, or about 30 minutes, or about 35 minutes, or about 40 minutes, or about 45 minutes, or about 50 minutes, or about 55 minutes, or about 60 minutes, or about 65 minutes, or about 70 minutes, or about 75 minutes, or about 80 minutes, or about 85 minutes, or about 90 minutes, or about 180.

In certain embodiments, the allantoamnion membrane is dried for 1 hour. In other embodiments, the allantoamnion membrane is dried for about 15 minutes, or about 30 minutes, or about 45 minutes, or about 60 minutes, or about 75 minutes, or about 90 minutes, or about 105 minutes, or about 2 hours, or about 2.25 hours, or about 2.5 hours, or about 2.75 hours, or about 3 hours. In some embodiments, the allantoamnion membrane is dried for more than 3 hours. In some embodiments, the allantoamnion membrane is air dried. In other embodiments, the allantoamnion membrane is air dried at room temperature.

In certain embodiments, the equine-specific therapeutic composition produced has a ratio of 2 $cm^2/mL$ of working solution. In other embodiments, the equine-specific therapeutic composition produced has a ratio of about 0.25 $cm^2/mL$ of working solution, or about 0.5 $cm^2/mL$ of working solution, or about 1.0 $cm^2/mL$ of working solution, or about 1.5 $cm^2/mL$ of working solution, or about 2.0 $cm^2/mL$ of working solution, or about 2.5 cm 2/mL of working solution, or about 3.0 $cm^2/mL$ of working solution, or about 3.5 $cm^2/mL$ of working solution, or about 4.0 $cm^2/mL$ of working solution, or about 4.5 $cm^2/mL$ of working solution, or about 5.0 $cm^2/mL$ of working solution, or about 7.5 $cm^2/mL$ of working solution, or about 10.0 $cm^2/mL$ of working solution, or about 12.5 $cm^2/mL$ of working solution, or about 15.0 $cm^2/mL$ of working solution, or about 17.5 $cm^2/mL$ of working solution, or about 20.0 $cm^2/mL$ of working solution, or about 22.5 $cm^2/mL$ of working solution, or about 25.0 $cm^2/mL$ of working solution, or about 27.5 $cm^2/mL$ of working solution, or about 30.0 $cm^2/mL$ of working solution. In further embodiments, the equine-specific therapeutic composition produced has a ratio of about 40 $cm^2/mL$ of working solution, or about 45 $cm^2/mL$ of working solution, or about 50 $cm^2/mL$ of working solution, or about 55 $cm^2/mL$ of working solution, or about 60 $cm^2/mL$ of working solution, or about 65 $cm^2/mL$ of working solution, or about 70 $cm^2/mL$ of working solution, or about 75 cm 2/mL of working solution, or about 80 $cm^2/mL$ of working solution, or about 85 $cm^2/mL$ of working solution, or about 90 $cm^2/mL$ of working solution, or about 95 $cm^2/mL$ of working solution, or about 100 $cm^2/mL$ of working solution.

As used herein, the term "about" refers to plus or minus 10% of the referenced number.

Although there has been shown and described the preferred embodiment of the present invention, it will be readily apparent to those skilled in the art that modifications may be made thereto that do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only, and the claims are not limited by the dimensions of the figures. In some embodiments, descriptions of the inventions described herein using the phrase "comprising" include embodiments that could be described as "consisting essentially of" or "consisting of," and as such, the written description requirement for claiming one or more embodiments of the present invention using the phrase "consisting essentially of" or "consisting of" is met.

Embodiments

The following embodiments are intended to be illustrative only and not to be limiting in any way.

Embodiment 1: An equine-specific therapeutic composition comprising: a) an equine-specific allantoamnion membrane comprising allantoamnion specific postbiotics; and b) a carrier solution, wherein the carrier solution comprises equine-specific amniotic fluid comprising amniotic fluid specific postbiotics.

Embodiment 2: The composition of embodiment 1, wherein the allantoamnion membrane further comprises allantoamnion membrane particles.

Embodiment 3: The composition of embodiment 2, wherein allantoamnion membrane particles are micronized (e.g., the equine-specific therapeutic composition comprises micronized allantoamnion membrane particles).

Embodiment 4: The composition of any one of embodiments 1-3 further comprising a chorioallantois membrane, an umbilical cord, Wharton's Jelly, an allantoic fluid, or a combination thereof.

Embodiment 5: The composition of embodiment 4, wherein the chorioallantois membrane comprises chorioallantois membrane particles.

Embodiment 6: The composition of embodiment 5, wherein the chorioallantois membrane particles are micronized (e.g., the equine-specific therapeutic composition comprises micronized chorioallantois membrane particles).

Embodiment 7: The composition of any one of embodiments 1-6 further comprising proteins, growth factors, cytokines, peptides, lipids, exosomes, nucleic acids, DNA, mRNA, and miRNA derived from the amniotic fluid, allantoic fluid, or a combination thereof.

Embodiment 8: The composition of any one of embodiments 1-7, further comprising proteins, growth factors, cytokines, peptides, lipids, exosomes, nucleic acids, DNA, mRNA, and miRNA derived from allantoamnion membrane particles, chorioallantois membrane particles, umbilical cord, Wharton's Jelly or a combination thereof.

Embodiment 9a: The composition of embodiment 7 or embodiment 8, wherein the proteins have anti-inflammatory properties, antifibrotic properties, antimicrobial properties, healing properties, repairing properties, immunoregulatory properties, anti-cancer properties, or a combination thereof.

Embodiment 9b: The composition of embodiment 7 or embodiment 8, wherein the exosomes have anti-inflammatory properties, antifibrotic properties, antimicrobial properties, healing properties, repairing properties, immunoregulatory properties, anti-cancer properties, or a combination thereof.

Embodiment 10: The composition of any one of embodiments 7-9, wherein the proteins are selected from a group comprising: IL1-ra, IL-1a, IL-1b, IL-2, IL-4, IL-6, IL-8, IL-10, MCP-1, VEGF, TIMP-1, TIMP-2, TIMP-3, TIMP-4, IGF, EGF, FGF, TGFb1, alpha-2-microglobulin, hyaluronic acid, proteoglycans, collagen, fibronectin, laminin and the like.

Embodiment 11: The composition of any one of embodiments 1-10, wherein the composition is free or substantially free of contaminants.

Embodiment 12: The composition of embodiment 11, wherein the contaminants are selected from a group comprising blood-related components, immunogenic blood-related components, microorganisms, fungi, yeast, or a combination thereof.

Embodiment 13: The composition of embodiment 12, wherein the blood-related components comprise plasma, red blood cells, white blood cells, platelets, wastes, or a combination thereof.

Embodiment 14: The composition of embodiment 12, wherein the microorganisms comprise bacteria, viruses, or a combination thereof.

Embodiment 15: The composition of embodiment 11, wherein the contaminants comprise byproducts of hemoglobin metabolism and/or catabolism, products of hemoglobin breakdown, or a combination thereof.

Embodiment 16: The composition of any one of embodiments 1-15, wherein the composition is free or substantially free of blood vessels.

Embodiment 17: The composition of any one of embodiments 1-16, wherein the allantoamnion membrane is free or substantially free of viable microorganisms.

Embodiment 18: The composition of any one of embodiments 1-17, wherein the amniotic fluid is free or substantially free of viable microorganisms.

Embodiment 19: The composition of any one of embodiments 1-18, wherein the postbiotics comprise metabolites of non-viable or viable microorganisms or their derivatives, or fragments of non-viable or viable microorganisms or their derivatives, or combinations thereof.

Embodiment 20: The composition of any one of embodiments 1-19, wherein the postbiotics comprise anti-inflammatory properties, antifibrotic properties, antimicrobial properties, antiatherosclerotic properties, autophagy, healing properties, repairing properties, immunoregulatory properties, anti-cancer properties, or a combination thereof.

Embodiment 21: The composition of any one of embodiments 1-20, further comprising cell free supernatants, biopolymers (e.g., exopolysaccharides), enzymes (e.g., antioxidant enzymes such as glutathione peroxidase, peroxide dismutase, catalase, and NADH-oxidase), cell wall fragments (including lipoteichoic acid), short-chain fatty acids (e.g., acetate, propionate, butyrate), bacterial lysates, or a combination thereof.

Embodiment 22: The composition of any one of embodiments 1-21, wherein the composition is physiologically and biologically active.

Embodiment 23: The composition of any one of embodiments 1-22, wherein the composition is administered via an injection, topically, or by inhalation.

Embodiment 24: The method of embodiment 23, wherein the composition is injected intravenously, intraarterially, intraarticularly, periarticularly, intramuscularly, subcutaneously, subconjunctivally, or via an intraligamentary, periligamentary, peritendinous, or intratendinous injection.

Embodiment 25: The composition of any one of embodiments 1-24, wherein the composition is used to treat cancer, benign tumors, joint diseases, joint injuries, soft tissue lesions, tendon lesions, ligament lesions, inflammatory diseases, respiratory diseases, immunological diseases, neurological diseases, skin wounds, ocular wounds, coronary wounds, nerve injuries, spinal injuries, muscle tears or organ diseases in individuals in need thereof.

Embodiment 26: The composition of embodiment 25, wherein skin wounds comprise burns, necrosis, scarring, skin ulcers and venous ulcers; wherein ocular wounds comprise glaucoma, ocular ulcers, corneal ulcers, conjunctival scleral or lid and orbital rim reconstruction; wherein coronary wounds comprise coronary bypass, heart valve repair and replacement, vein repair and artery repair.

Embodiment 27: The composition of embodiment 25 or embodiment 26, wherein the individual is an equine, dog, cat, pig, cow, camel, or human.

Embodiment 28: The composition of any one of embodiments 1-27, wherein the composition is used for skin repair, ocular repair, or coronary repair.

Embodiment 29: A method of treating and/or preventing cancer in an individual, the method comprising administering a therapeutic amount of a composition according to any one of embodiments 1-24, to the individual (e.g., an equine) in need thereof. The individual may be an equine, dog, cat, pig, cow, camel, or human.

Embodiment 30: A method of producing an equine-specific therapeutic composition, the method comprising: a) obtaining an equine-specific allantoamnion membrane and equine-specific amniotic fluid; b) processing the equine-specific allantoamnion membrane and the equine-specific amniotic fluid; wherein processing the equine-specific allantoamnion membrane comprises decontaminating and micronizing the allantoamnion membrane and wherein processing the equine specific amniotic fluid comprises decontaminating the amniotic fluid; and c) resuspending the micronized allantoamnion membrane into a carrier solution comprising the processed amniotic fluid to produce the equine specific therapeutic composition.

Embodiment 31: The method of embodiment 30, wherein obtaining the allantoamnion membrane and the amniotic fluid comprises obtaining a whole equine placenta, wherein the whole equine placenta is dissected to obtain the allantoamnion membrane.

Embodiment 32: The method embodiment 31, wherein the allantoamnion membrane is dissected to retain all layers of the allantoamnion membrane.

Embodiment 33: The method embodiment 31, wherein the allantoamnion membrane is dissected to retain one or more layers of the allantoamnion membrane.

Embodiment 34: The method embodiment 31, wherein the allantoamnion membrane is dissected to retain two or more layers of the allantoamnion membrane.

Embodiment 35: The method of any one of embodiments 30-34, wherein decontaminating the allantoamnion membrane comprises removing contaminants from the allantoamnion membrane.

Embodiment 36: The method embodiment 35, wherein the contaminants are selected from a group comprising blood-related components, immunogenic blood-related components, microorganisms, fungi, yeast, or a combination thereof.

Embodiment 37: The method embodiment 36, wherein the blood-related components comprise plasma, red blood cells, white blood cells, platelets, wastes, or a combination thereof Embodiment 38: The method embodiment 36, wherein the microorganisms comprise bacteria, viruses, or a combination thereof.

Embodiment 39: The method embodiment 35, wherein the contaminants comprise byproducts of hemoglobin metabolism and/or catabolism, products of hemoglobin breakdown, or a combination thereof.

Embodiment 40: The method of any one of embodiments 30-39, wherein decontaminating the allantoamnion membrane comprises partially removing blood vessels from the allantoamnion membrane.

Embodiment 41: The method of any one of embodiments 30-40, wherein decontaminating the allantoamnion membrane comprises removing blood vessels from the allantoamnion membrane.

Embodiment 42: The method of any one of embodiments 30-41, wherein processing the allantoamnion membrane further comprises rinsing and drying the allantoamnion membrane.

Embodiment 43: The method of embodiment 42, wherein the allantoamnion membrane is rinsed once.

Embodiment 44: The method of embodiment 42, wherein the allantoamnion membrane is rinsed twice.

Embodiment 45: The method of any one of embodiments 30-44, wherein micronizing allantoamnion membrane produces allantoamnion membrane particles.

Embodiment 46: The method of embodiment 45, wherein the allantoamnion membrane particles are produced by cryofracturing the allantoamnion membrane.

Embodiment 47: The method of embodiment 45 or embodiment 46, wherein the allantoamnion membrane particles are resuspended in the carrier solution comprising the processed amniotic fluid to produce the equine-specific therapeutic composition.

Embodiment 48: The method of any one of embodiments 30-47, further comprising freezing the equine-specific therapeutic composition.

Embodiment 49: The method of embodiment 48, wherein freezing the equine-specific therapeutic composition preserves proteins and biocomponents.

Embodiment 50: The method of any one of embodiments 30-49, further comprising lyophilizing the equine-specific therapeutic composition.

Embodiment 51: The method of any one of embodiments 30-50, wherein the equine-specific therapeutic composition is stored at refrigerator temperature (e.g., at or below about 5° C.).

Embodiment 52: The method of any one of embodiments 30-50, wherein the equine-specific therapeutic composition is stored at room temperature (e.g., about 15 to 25° C.).

Embodiment 53: The method of any one of embodiments 30-52, wherein the method retains postbiotics, proteins, growth factors, cytokines, peptides, lipids, exosomes, nucleic acids, DNA, mRNA, or miRNA derived from the amniotic fluid.

Embodiment 54: The method of any one of embodiments 30-53, wherein the method retains postbiotics, proteins, growth factors, cytokines, peptides, lipids, exosomes, nucleic acids, DNA, mRNA, and miRNA derived from allantoamnion membrane.

Embodiment 55: A method of producing an equine-specific therapeutic composition, the method comprising: a) obtaining a whole equine placenta comprising an allantoamnion membrane and amniotic fluid; b) dissecting the whole equine placenta and retaining one or more layers of the allantoamnion membrane; c) processing the allantoamnion membrane and the amniotic fluid; wherein processing the allantoamnion membrane comprises decontaminating and micronizing the allantoamnion membrane and wherein processing the amniotic fluid comprising decontaminating the amniotic fluid, and d) resuspending the micronized allantoamnion membrane into a carrier solution comprising the processed amniotic fluid to produce the equine specific therapeutic composition.

Embodiment 56: The method of embodiment 55, further comprising retaining the allantoamnion membrane to retain all layers of the allantoamnion membrane.

Embodiment 57: The method of embodiment 55 or embodiment 56, further comprising freezing the equine-specific therapeutic composition.

Embodiment 58: The method of any one of embodiments 55-58, wherein decontaminating the allantoamnion membrane comprises removing contaminants from the allantoamnion membrane.

Embodiment 59: The method embodiment 58, wherein the contaminants are selected from a group comprising blood-related components, immunogenic blood-related components, microorganisms, fungi, yeast, or a combination thereof.

Embodiment 60: The method embodiment 59, wherein the blood-related components comprise plasma, red blood cells, white blood cells, platelets, wastes, or a combination thereof.

Embodiment 61: The method embodiment 59, wherein the microorganisms comprise bacteria, viruses, or a combination thereof.

Embodiment 62: The method embodiment 58, wherein the contaminants comprise byproducts of hemoglobin metabolism and/or catabolism, products of hemoglobin breakdown, or a combination thereof Embodiment 63: The method of any one of embodiments 55-62, wherein decontaminating the allantoamnion membrane comprises partially removing blood vessels from the allantoamnion membrane.

Embodiment 64: The method of any one of embodiments 55-63, wherein decontaminating the allantoamnion membrane comprises removing blood vessels from the allantoamnion membrane.

Embodiment 65: The method of any one of embodiments 55-64, wherein processing the allantoamnion membrane further comprises rinsing and drying the allantoamnion membrane.

Embodiment 66: The method of embodiment 65, wherein the allantoamnion membrane is rinsed once.

Embodiment 67: The method of embodiment 65, wherein the allantoamnion membrane is rinsed twice.

Embodiment 68: The method of any one of embodiments 55-67, wherein micronizing allantoamnion membrane produces allantoamnion membrane particles.

Embodiment 69: The method of embodiment 68, wherein the allantoamnion membrane particles are produced by cryofracturing the allantoamnion membrane.

Embodiment 70: The method of embodiment 68 or 69, wherein the allantoamnion membrane particles are resuspended in the carrier solution comprising the processed amniotic fluid to produce the equine-specific therapeutic composition.

Embodiment 71: The method of any one of embodiments 55-70, further comprising freezing the equine-specific therapeutic composition.

Embodiment 72: The method of embodiment 71, wherein freezing the equine-specific therapeutic composition preserves proteins and biocomponents.

Embodiment 73: The method of any one of embodiments 55-72, further comprising lyophilizing the equine-specific therapeutic composition.

Embodiment 74: The method of any one of embodiments 55-73, wherein the equine-specific therapeutic composition is stored at refrigerator temperature (e.g., at or below about 5° C.).

Embodiment 75: The method of any one of embodiments 55-73, wherein the equine-specific therapeutic composition is stored at room temperature (e.g., about 15 to 25° C.).

Embodiment 76: The method of any one of embodiments 55-75, wherein the method retains postbiotics, proteins, growth factors, cytokines, peptides, lipids, exosomes, nucleic acids, DNA, mRNA, or miRNA derived from the amniotic fluid.

Embodiment 77: The method of any one of embodiments 55-76, wherein the method retains postbiotics, proteins, growth factors, cytokines, peptides, lipids, exosomes, nucleic acids, DNA, mRNA, and miRNA derived from allantoamnion membrane.

Embodiment 78: The method of any one of embodiments 30-77, wherein the equine-specific therapeutic composition has a ratio of 0.25 $cm^2$/mL to 30 $cm^2$/mL of working solution Embodiment 79: The method of any one of embodiments 30-78, wherein the equine-specific therapeutic composition has a ratio of 1.0 $cm^2$/mL to 5.0 $cm^2$/mL of working solution.

Embodiment 80: A method of treating cancer in an individual, the method comprising administering to the individual in need thereof a therapeutic amount of equine-specific therapeutic composition comprising: a) an equine-specific allantoamnion membrane comprising allantoamnion specific postbiotics; and b) a carrier solution, wherein the carrier solution comprises equine-specific amniotic fluid comprising amniotic specific postbiotics.

Embodiment 81: A method of preventing cancer in an individual, the method comprising administering to the individual in need thereof a therapeutic amount of equine-specific therapeutic composition comprising: a) an equine-specific allantoamnion membrane comprising allantoamnion specific postbiotics; and b) a carrier solution, wherein the carrier solution comprises equine-specific amniotic fluid comprising amniotic specific postbiotics.

Embodiment 82: The method of embodiment 80 or embodiment 81, wherein the individual is an equine.

Embodiment 83: A method of treating cancer in an equine, the method comprising administering to the equine in need thereof a therapeutic amount of equine-specific therapeutic composition comprising: a) an equine-specific allantoamnion membrane comprising allantoamnion specific postbiotics; and b) a carrier solution, wherein the carrier solution comprises equine-specific amniotic fluid comprising amniotic specific postbiotics.

Embodiment 84: A method of preventing cancer in an equine, the method comprising administering to the equine in need thereof a therapeutic amount of equine-specific therapeutic composition comprising: a) an equine-specific allantoamnion membrane comprising allantoamnion specific postbiotics; and b) a carrier solution, wherein the carrier solution comprises equine-specific amniotic fluid comprising amniotic specific postbiotics.

Embodiment 85: A method of treating a joint disease in an individual, the method comprising administering to the individual in need thereof a therapeutic amount of equine-specific therapeutic composition comprising: a) an equine-specific allantoamnion membrane comprising allantoamnion specific postbiotics; and b) a carrier solution, wherein the carrier solution comprises equine-specific amniotic fluid comprising amniotic specific postbiotics.

Embodiment 86: A method of treating a joint injury in an individual, the method comprising administering to the individual in need thereof a therapeutic amount of equine-specific therapeutic composition comprising: a) an equine-specific allantoamnion membrane comprising allantoamnion specific postbiotics; and b) a carrier solution, wherein the carrier solution comprises equine-specific amniotic fluid comprising amniotic specific postbiotics.

Embodiment 87: A method of treating a soft tissue injury in an individual, the method comprising administering to the individual in need thereof a therapeutic amount of equine-specific therapeutic composition comprising: a) an equine-specific allantoamnion membrane comprising allantoamnion specific postbiotics; and b) a carrier solution, wherein the carrier solution comprises equine-specific amniotic fluid comprising amniotic specific postbiotics.

Embodiment 88: The method of any one of embodiments 83-87, wherein the individual is an equine.

Embodiment 89: A method of treating a joint disease in an equine, the method comprising administering to the equine in need thereof a therapeutic amount of equine-specific therapeutic composition comprising: a) an equine-specific allantoamnion membrane comprising allantoamnion specific proteins and postbiotics; and b) a carrier solution, wherein the carrier solution comprises equine-specific amniotic fluid comprising amniotic specific proteins and postbiotics.

Embodiment 90: A method of treating a joint injury in an equine, the method comprising administering to the equine in need thereof a therapeutic amount of equine-specific therapeutic composition comprising: a) an equine-specific allantoamnion membrane comprising allantoamnion specific proteins and postbiotics; and b) a carrier solution, wherein the carrier solution comprises equine-specific amniotic fluid comprising amniotic specific proteins and postbiotics.

Embodiment 91: A method of treating a soft tissue injury in an equine, the method comprising administering to the equine in need thereof a therapeutic amount of equine-specific therapeutic composition comprising: a) an equine-specific allantoamnion membrane comprising allantoamnion specific proteins and postbiotics; and b) a carrier solution, wherein the carrier solution comprises equine-specific amniotic fluid comprising amniotic specific proteins and postbiotics.

Embodiment 92: The method of any one of embodiment 80-91, wherein the allantoamnion membrane further comprises allantoamnion membrane particles, wherein allantoamnion membrane particles are micronized (e.g., the equine-specific therapeutic composition comprises micronized allantoamnion membrane particles).

Embodiment 93: The method of any one of embodiment 80-92, wherein the equine-specific therapeutic composition further comprises a chorioallantois membrane, an umbilical cord, Wharton's Jelly, an allantoic fluid, or a combination thereof.

Embodiment 94: The method of embodiment 93, wherein the chorioallantois membrane comprises chorioallantois membrane particles, wherein the chorioallantois membrane particles are micronized (e.g., the equine-specific therapeutic composition comprises micronized chorioallantois membrane particles).

Embodiment 95: The method of any one of embodiment 80-94, wherein the equine-specific therapeutic composition further comprises proteins, growth factors, cytokines, peptides, lipids, exosomes, nucleic acids, DNA, mRNA, and miRNA derived from the amniotic fluid, allantoic fluid, or a combination thereof.

Embodiment 96: The method of any one of embodiment 80-95, wherein the equine-specific therapeutic composition further comprises proteins, growth factors, cytokines, peptides, lipids, exosomes, nucleic acids, DNA, mRNA, and miRNA derived from allantoamnion membrane particles, chorioallantois membrane particles, umbilical cord, Wharton's Jelly or a combination thereof.

Embodiment 97a: The method of embodiment 95 or embodiment 96, wherein the proteins have anti-inflammatory properties, antifibrotic properties, antimicrobial properties, healing properties, repairing properties, immunoregulatory properties, anti-cancer properties, or a combination thereof.

Embodiment 97b: The method of embodiment 95 or embodiment 96, wherein the exosomes have anti-inflammatory properties, antifibrotic properties, antimicrobial properties, healing properties, repairing properties, immunoregulatory properties, anti-cancer properties, or a combination thereof.

Embodiment 98: The method of any one of embodiments 95-97, wherein the proteins are selected from a group comprising: IL1-ra, IL-1a, IL-1b, IL-2, IL-4, IL-6, IL-8, IL-10, MCP-1, VEGF, TIMP-1, TIMP-2, TIMP-3, TIMP-4, IGF, EGF, FGF, TGFb1, alpha-2-microglobulin, hyaluronic acid, proteoglycans, collagen, fibronectin, laminin and the like.

Embodiment 99: The method of any one of embodiment 80-98, wherein the composition is free or substantially free of contaminants.

Embodiment 100: The method of embodiment 99, wherein the contaminants are selected from a group comprising blood-related components, immunogenic blood-related components, microorganisms, fungi, yeast, or a combination thereof.

Embodiment 101: The method of embodiment 100, wherein the blood-related components comprise plasma, red blood cells, white blood cells, platelets, wastes, or a combination thereof.

Embodiment 102: The method of embodiment 100, wherein the microorganisms comprise bacteria, viruses, or a combination thereof.

Embodiment 103: The method of embodiment 99, wherein the composition is free or substantially free of blood vessels.

Embodiment 104: The method of any one of embodiments 80-103, wherein the allantoamnion membrane is free or substantially free of viable microorganisms.

Embodiment 105: The method of any one of embodiments 80-104, wherein the amniotic fluid is free or substantially free of viable microorganisms.

Embodiment 106: The method of any one of embodiments 80-105, wherein the postbiotics comprise metabolites and fragments of non-viable microorganisms or their derivatives.

Embodiment 107: The method of any one of embodiments 80-106, wherein the postbiotics have anti-inflammatory properties, antifibrotic properties, antimicrobial properties, antiatherosclerotic properties, autophagy, healing properties, repairing properties, immunoregulatory properties, anti-cancer properties, or a combination thereof.

Embodiment 108: The method of any one of embodiments 80-107, wherein the composition further comprises cell free supernatants, biopolymers (e.g., exopolysaccharides), enzymes (e.g., antioxidant enzymes such as glutathione peroxidase, peroxide dismutase, catalase and NADH-oxidase), cell wall fragments (including lipoteichoic acid), short-chain fatty acids (e.g., acetate, propionate, butyrate), bacterial lysates, or a combination thereof.

Embodiment 109: The method of any one of embodiments 80-108, wherein the composition is physiologically and biologically active.

Embodiment 110: The method of any one of embodiments 80-109, wherein the composition is administered via an injection, topically, or by inhalation.

Embodiment 111: The method of any one of embodiments 80-109, wherein the composition is injected intravenously, intraarterially, intra-articularly, periarticularly, intramuscularly, subcutaneously, subconjunctivally, or via a intraligamentary, perilagamentary, peritendinous, or intratendinous injection.

Embodiment 112: A equine-specific therapeutic composition for use in a method of treating cancer in an individual (e.g., an equine), the composition comprising: comprising: a) an equine-specific allantoamnion membrane comprising allantoamnion specific postbiotics; and b) a carrier solution, wherein the carrier solution comprises equine-specific amniotic fluid comprising amniotic specific postbiotics.

Embodiment 113: A equine-specific therapeutic composition for use in a method of preventing cancer in an individual (e.g., an equine), the composition comprising: comprising: a) an equine-specific allantoamnion membrane comprising allantoamnion specific postbiotics; and b) a carrier solution, wherein the carrier solution comprises equine-specific amniotic fluid comprising amniotic specific postbiotics.

Embodiment 114: A equine-specific therapeutic composition for use in a method of treating a joint disease in an individual (e.g., an equine), the composition comprising: comprising: a) an equine-specific allantoamnion membrane comprising allantoamnion specific postbiotics; and b) a carrier solution, wherein the carrier solution comprises equine-specific amniotic fluid comprising amniotic specific postbiotics.

Embodiment 115: A equine-specific therapeutic composition for use in a method of treating a joint injury in an individual (e.g., an equine), the composition comprising: comprising: a) an equine-specific allantoamnion membrane comprising allantoamnion specific postbiotics; and b) a carrier solution, wherein the carrier solution comprises equine-specific amniotic fluid comprising amniotic specific postbiotics.

Embodiment 116: A equine-specific therapeutic composition for use in a method of treating a soft tissue injury in an individual (e.g., an equine), the composition comprising: comprising: a) an equine-specific allantoamnion membrane comprising allantoamnion specific postbiotics; and b) a carrier solution, wherein the carrier solution comprises equine-specific amniotic fluid comprising amniotic specific postbiotics.

What is claimed is:

1. A therapeutic composition comprising:

a. a micronized allantoamnion membrane comprising allantoamnion specific postbiotics; and b. a carrier solution, wherein the carrier solution comprises amniotic fluid comprising amniotic fluid specific postbiotics.

2. The composition of claim 1, wherein the micronized allantoamnion membrane comprises an equine-specific micronized allantoamnion membrane, and the amniotic fluid comprises an equine-specific amniotic fluid.

3. The composition of claim 1, further comprising a chorioallantois membrane, an umbilical cord, Wharton's Jelly, an allantoic fluid, or a combination thereof.

4. The composition of claim 3, wherein the chorioallantois membrane comprises chorioallantois membrane particles, wherein the chorioallantois membrane particles are micronized.

5. The composition of claim 1, further comprising proteins, growth factors, cytokines, peptides, lipids, exosomes, nucleic acids, DNA, mRNA, and miRNA derived from allantoamnion membrane particles, chorioallantois membrane particles, umbilical cord, Wharton's Jelly or a combination thereof.

6. The composition of claim 1, further comprising proteins, growth factors, cytokines, peptides, lipids, exosomes, nucleic acids, DNA, mRNA, and miRNA derived from the amniotic fluid, allantoic fluid, or a combination thereof.

7. The composition of claim 1, wherein the composition is free or substantially free of contaminants or blood vessels.

8. The composition of claim 7, wherein the contaminants are selected from a group comprising blood-related components, immunogenic blood-related components, microorganisms, fungi, or a combination thereof.

9. The composition of claim 8, wherein the blood-related components comprise plasma, red blood cells, white blood cells, platelets, wastes, or a combination thereof.

10. The composition of claim 7, wherein the contaminants comprise byproducts of hemoglobin metabolism and/or catabolism, products of hemoglobin breakdown, or a combination thereof.

11. The composition of claim 1, wherein the micronized allantoamnion membrane and/or the amniotic fluid is free or substantially free of viable microorganisms.

12. The composition of claim 1, wherein the micronized allantoamnion membrane and/or the amniotic fluid is free or substantially free of non-viable microorganisms.

13. The composition of claim 1, wherein the micronized allantoamnion membrane and/or the amniotic fluid comprise non-viable microorganisms.

14. The composition of claim 1, wherein the postbiotics comprise metabolites of non-viable or viable microorganisms or their derivatives, or fragments of non-viable or viable microorganisms or their derivatives, or combinations thereof.

15. The composition of claim 1, further comprising cell-free supernatants, biopolymers, enzymes, cell wall fragments, short-chain fatty acids, bacterial lysates, or a combination thereof.

16. A method of treating cancer in an individual, the method comprising administering to the individual in need thereof a therapeutic amount of equine-specific therapeutic composition comprising:

a. an equine-specific micronized allantoamnion membrane comprising allantoamnion specific postbiotics; and b. a carrier solution, wherein the carrier solution comprises equine-specific amniotic fluid comprising amniotic specific postbiotics.

17. A method of producing an equine-specific therapeutic composition, the method comprising:

a. obtaining an equine-specific allantoamnion membrane and equine-specific amniotic fluid;

b. processing the equine-specific allantoamnion membrane and the equine-specific amniotic fluid; wherein processing the equine-specific allantoamnion membrane comprises decontaminating and micronizing the allantoamnion membrane and wherein processing the equine specific amniotic fluid comprises decontaminating the amniotic fluid; and c. resuspending the micronized allantoamnion membrane into a carrier solution comprising the processed amniotic fluid to produce the equine specific therapeutic composition.

18. The method of claim 17, wherein micronizing the allantoamnion membrane produces allantoamnion membrane particles.

19. The method of claim 17, wherein the method retains postbiotics, proteins, growth factors, cytokines, peptides, lipids, exosomes, mRNA, or miRNA derived from the allantoamnion membrane, the amniotic fluid or both.

* * * * *